(12) United States Patent
Foda et al.

(10) Patent No.: US 11,639,244 B2
(45) Date of Patent: May 2, 2023

(54) DEVICE FOR SANITARY DRAINAGE OF AN OSTOMY POUCH

(71) Applicants: Mohamed M. R. Foda, Coquitlam (CA); Aisha M. K. Monib, Coquitlam (CA)

(72) Inventors: Mohamed M. R. Foda, Coquitlam (CA); Aisha M. K. Monib, Coquitlam (CA)

( * ) Notice: Subject to any disclaimer, the term of this patent is extended or adjusted under 35 U.S.C. 154(b) by 432 days.

(21) Appl. No.: 17/053,084

(22) PCT Filed: May 8, 2019

(86) PCT No.: PCT/CA2019/050611
§ 371 (c)(1),
(2) Date: Nov. 5, 2020

(87) PCT Pub. No.: WO2019/213762
PCT Pub. Date: Nov. 14, 2019

(65) Prior Publication Data
US 2021/0070488 A1    Mar. 11, 2021

Related U.S. Application Data

(60) Provisional application No. 62/669,542, filed on May 10, 2018.

(51) Int. Cl.
| | | |
|---|---|---|
| *B65B 69/00* | (2006.01) | |
| *A61F 5/445* | (2006.01) | |
| *E03D 13/00* | (2006.01) | |
| *E03D 11/02* | (2006.01) | |

(52) U.S. Cl.
CPC ......... *B65B 69/0016* (2013.01); *A61F 5/445* (2013.01); *E03D 11/025* (2013.01); *E03D 13/00* (2013.01)

(58) Field of Classification Search
CPC ....... E03D 11/025; E03D 13/00; A61F 5/445; B65B 69/0016
USPC ............................................................ 4/300
See application file for complete search history.

(56) References Cited

U.S. PATENT DOCUMENTS

| | | | | |
|---|---|---|---|---|
| 2,568,857 A | * | 9/1951 | Jacobs ................... | A61F 5/442 604/277 |
| 2,664,573 A | * | 1/1954 | Taylor .................... | A61F 5/445 4/661 |
| 2,864,094 A | * | 12/1958 | Williams, Jr. ........... | A61G 9/00 D24/123 |
| 3,412,408 A | * | 11/1968 | Michal, Jr. ............. | E03D 11/025 4/301 |

(Continued)

*Primary Examiner* — Benjamin R Shaw
(74) *Attorney, Agent, or Firm* — McMillan LLP

(57) ABSTRACT

A device for the sanitary drainage of the contents of an ostomy pouch into a waste receptacle (e.g., toilet) is provided. The device includes a base; an extendible shaft coupled to the base; a body that receives the ostomy pouch while it is attached to a patient and directs the contents of the pouch into a chute; a pivoting mechanism that couples the body to the shaft to adjust the angle there between; and a chute coupled to the body that directs the contents of the ostomy pouch into the waste receptacle. The device and the adjustability that it provides offers patients, particularly mobile patients, the ability to sanitarily and ergonomically empty their ostomy pouches into a waste receptacle, such as a toilet, while in a standing position.

20 Claims, 13 Drawing Sheets

(56) References Cited

U.S. PATENT DOCUMENTS

| | | | | |
|---|---|---|---|---|
| 4,145,768 | A * | 3/1979 | Chevrette | E03D 13/00 |
| | | | | 4/144.1 |
| 4,282,611 | A * | 8/1981 | O'Day | E03D 11/025 |
| | | | | 4/144.1 |
| 4,285,076 | A | 8/1981 | Dickstein | |
| 9,194,115 | B1 * | 11/2015 | Green | E03D 13/00 |
| 9,605,420 | B1 | 3/2017 | Berger | |
| 9,637,906 | B1 * | 5/2017 | Charles | E03D 13/005 |
| 10,893,973 | B1 * | 1/2021 | Cordova | B08B 9/20 |
| 2006/0096016 | A1 * | 5/2006 | Krowl | E03D 11/025 |
| | | | | 4/341 |
| 2011/0296602 | A1 * | 12/2011 | Anderson | A47K 11/12 |
| | | | | 4/300.3 |
| 2012/0246816 | A1 * | 10/2012 | Jung | E03D 11/025 |
| | | | | 4/341 |
| 2014/0283292 | A1 * | 9/2014 | McKnight | E03D 13/002 |
| | | | | 4/309 |
| 2015/0000024 | A1 * | 1/2015 | Plath | A61F 5/4404 |
| | | | | 4/301 |
| 2015/0376888 | A1 * | 12/2015 | Chery | E03D 11/025 |
| | | | | 4/301 |
| 2021/0030220 | A1 * | 2/2021 | Green | A47K 17/00 |
| 2021/0070488 | A1 * | 3/2021 | Foda | E03D 13/00 |
| 2021/0262216 | A1 * | 8/2021 | Panseri | E03D 11/025 |

* cited by examiner

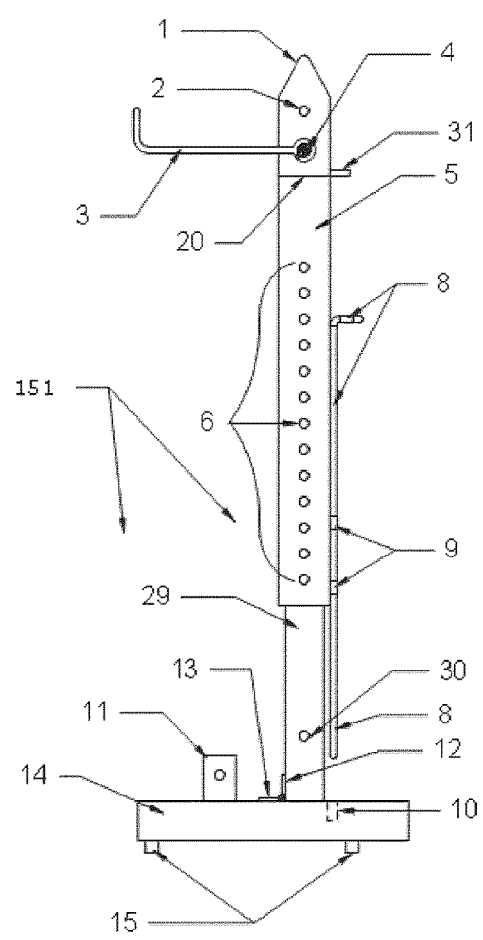
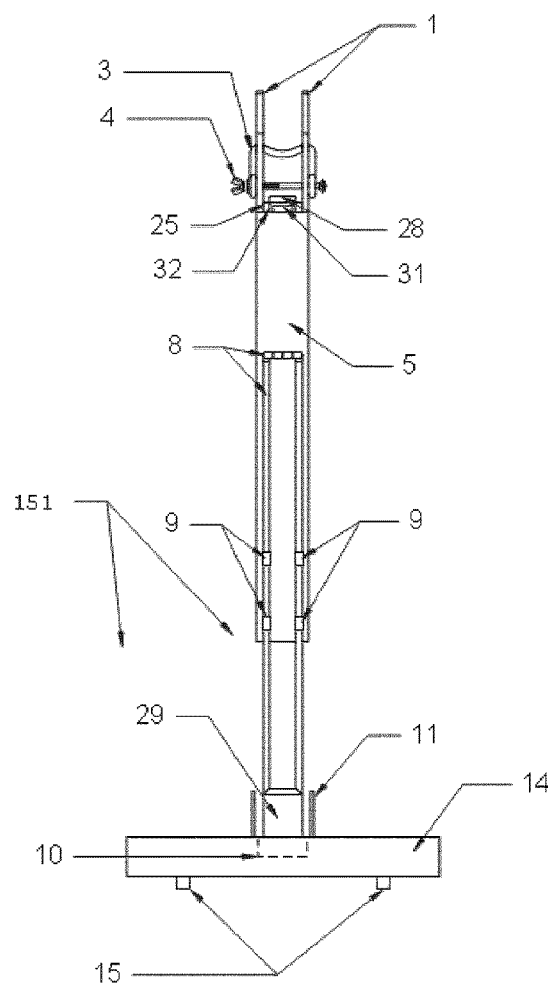
FIG. 03
FIG. 04

DEVICE FOR SANITARY DRAINAGE OF AN OSTOMY POUCH

CROSS-REFERENCE TO RELATED APPLICATIONS

This application is a national phase of Patent Cooperation Treaty (PCT) application No. PCT/CA2019/050611 having an international filing date of May 8, 2019. PCT application No. PCT/CA2019/050611 in turn claims priority from U.S. application No. 62/669,542 filed May 10, 2018. All of the applications referred to in this paragraph are hereby incorporated herein by reference.

FIELD

The present disclosure relates generally to drainage devices. More particularly, the present disclosure relates to a device for sanitary drainage of an ostomy pouch.

BACKGROUND

After intestinal or urinary diversion surgery, a patient is left with an abdominal wall opening (e.g., stoma; meaning mouth) that allows biological waste to flow out of the patient's body (e.g., ostomy). Commonly performed ostomies include: a colostomy (diversion of a colon to an abdominal wall surface); an ileostomy (diversion of a terminal end of a small intestine, the ileum, to an abdominal skin surface); and, an ileal conduit (urinary diversion using an isolated segment of the ileum after surgical removal of the bladder) ending in a urostomy.

There are a number of reasons for intestinal and urinary diversion surgeries, including cancers, traumatic injuries, inflammatory bowel diseases, and other intestinal or urinary tract pathologies. Depending on the condition of the patient and the nature of the disease, the created ostomy would either be temporary (surgically reversed after a period of time) or permanent.

Unlike normal intestinal and urinary tracts, an ostomy lacks sphincter control of the waste discharged out of the body. Following an ostomy surgery, patients require use of a pouch or bag attached to the abdomen around the stoma for collection and temporary storage of biological waste (stool or urine) until it is drained or discarded. Most commonly, the pouches used are drainable (e.g., not meant to be replaced after one use), and as such, require periodic emptying of accumulated waste when they are about one-third to half-full. Customarily, the collected waste in an ostomy pouch is emptied either directly into a waste disposal fixture (e.g. toilet), or into a waste-collection container, or a receptacle or other collection device.

Generally, collected biological waste in ostomy pouches is emptied either directly into a toilet, or into a waste-collection container or device. When emptying pouches directly into a toilet, an ostomy patient may have to stand over, or sit on a toilet (forward or backward), straddle a toilet, or kneel on the floor next to a toilet, to drain the pouch contents. Attempting to freely drain a pouch into a toilet from such positions can result in excessive biological waste soiling and splashing because of the physical gap between the ostomy pouch and the receiving toilet waterline. When a container is used, typically it is held close to a patient's ostomy pouch; alternatively, it may be attached to a front part of the toilet's rim at time of drainage, the filled container being emptied into a toilet, or disposed of later as garbage. Alternatively, an ostomy patient may use an accessory device designed to facilitate emptying an ostomy pouch into a toilet or waste-collection container while the patient is either in a sitting or standing position.

Improvements in devices for sanitary drainage of an ostomy pouch are desirable.

BRIEF DESCRIPTION OF THE DRAWINGS

Embodiments of the present disclosure will now be described, by way of example only, with reference to the attached Figures.

FIG. 03 depicts a side elevation view of Component I (the stand) of device 101 and device 201 for drainage of contents of an ostomy in accordance with embodiments of the present disclosure.

FIG. 04 depicts a rear elevation view of Component I (the stand) of device 101 and device 201 for drainage of contents of an ostomy pouch in accordance with embodiments of the present disclosure.

BRIEF SUMMARY

Figure 1:
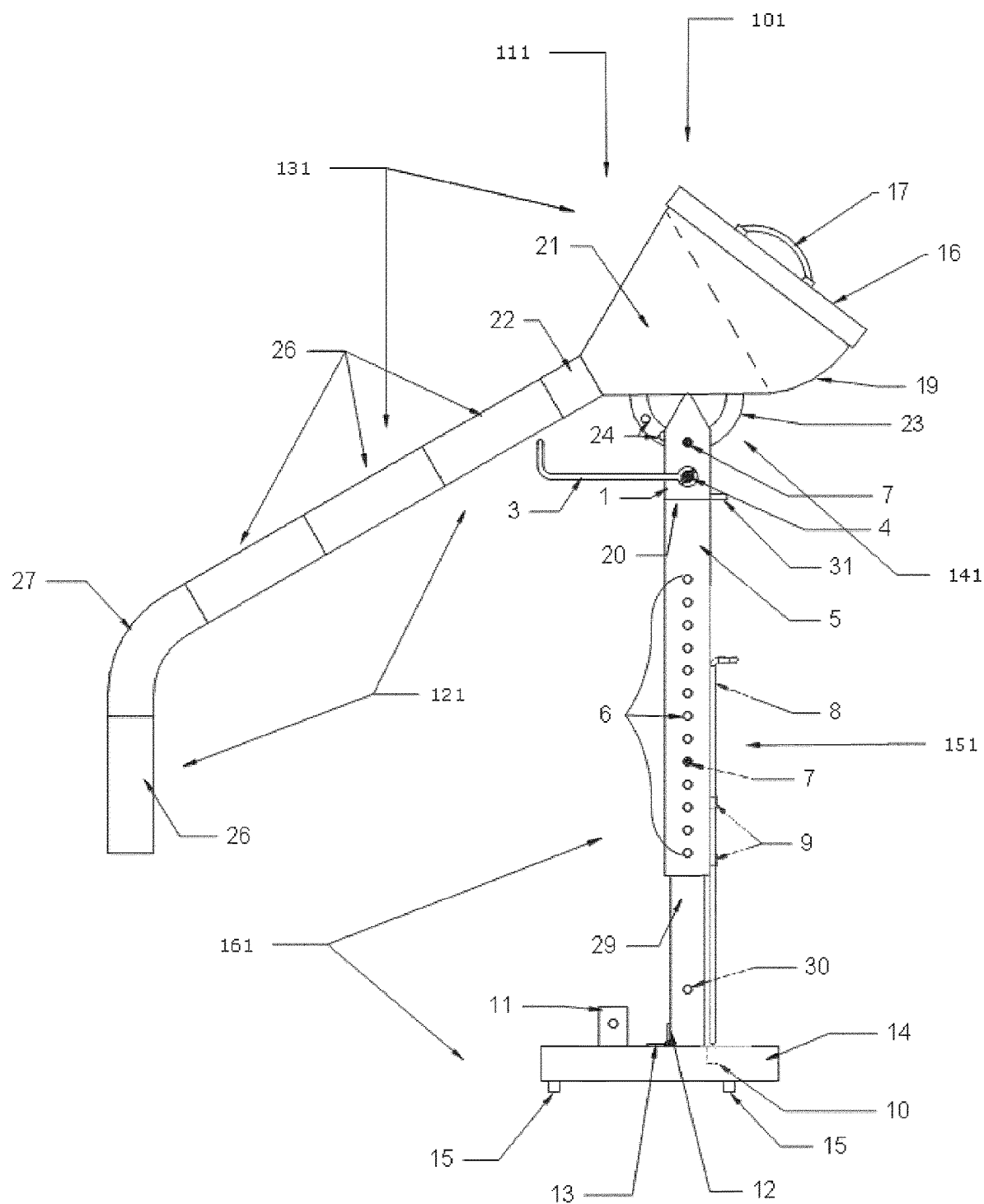
FIG. 01 depicts a side elevation view of device 101 for drainage of contents of an ostomy pouch, in accordance with an embodiment of the present disclosure.

The following presents a simplified summary of the disclosure in order to provide a basic understanding of some aspects of the disclosure. It is not intended to identify key or critical elements of the embodiments or to delineate the scope of the embodiments. The following summary merely presents some concepts of the disclosure in a simplified form as a prelude to the more detailed description provided below.

A device is provided for sanitary drainage of contents of an ostomy pouch into a receptacle, such as a toilet. In an aspect, the device comprises: a base; an extendible shaft configured to provide adjustment of a length of the shaft, the extendible shaft having a lower end coupled to the base and having an upper end; a body configured to receive the ostomy pouch while the pouch is attached to a mobile patient in an upright position, the body having an upper end defining a body inlet configured to receive the ostomy pouch, the body having a lower end defining a body outlet configured to direct the contents of the ostomy pouch out of the body; a pivoting mechanism pivotally coupling the lower end of body to the upper end of the extendible shaft, the pivoting mechanism engaging the body between the body inlet and the body outlet to provide adjustment of an angle between the body and the extendible shaft; and a chute coupled to the body outlet and configured to receive the contents of the ostomy pouch from the body and to direct the contents into the toilet while the pouch is attached to the mobile patient, the chute having an upper end coupled to the outlet end of the body, the upper end of the chute defining a chute inlet configured to direct the contents of the ostomy pouch into the chute, and having a lower end defining a chute outlet configured to direct the contents out of the chute and into the toilet while the pouch is attached to the mobile patient.

In an example implementation, the chute comprises an extendible chute. In an example implementation, the extendible chute comprises a plurality of chute segments coupled together via a plurality of chute joints to configure the chute to a pre-determined length. In an example implementation, the plurality of chute segments comprises a plurality of linear chute segments and an angled chute segment cooperating to provide a fixed angle between the upper end and the lower end of the chute.

In an example implementation, the shaft comprises at least two telescoping sleeves. In an example implementation, the at least two telescoping sleeves are configured to couple together at a plurality of engagement points.

In an example implementation, the pivoting mechanism comprises a handle defining a perforated curved track, the handle pivotally coupling the body to the upper end of the shaft. In an example implementation, the handle is configured to couple the upper end of the shaft at a plurality of engagement points.

In an example implementation, the upper end of the body defining the body inlet further defines a rim around the periphery of the body inlet that extends towards the center of the body, the rim being configured to obstruct splash-back of the contents of the ostomy pouch during drainage.

In an example implementation, the device further includes a lid configured to engage and cover the upper end of the body defining the body inlet.

In an example implementation, the device further includes a lever coupled to the upper end of the chute and the upper end of the shaft, the lever enabling further adjustment of an angle between the chute and the shaft.

In an example implementation, the shaft defines a plurality of slots, and the device further includes a moveable bracket attached to the extendible shaft to engage a slot in the base to secure the shaft in a vertical position when the device is in use In an example implementation, the device further includes a slidable lock assembly coupled to the upper end of the extendible shaft, the slidable lock assembly being configured to engage the moveable bracket and secure the moveable bracket in a position disengaged from the slot in the base.

In an example implementation, the base comprises two brackets fixed to an upper surface of the base. In an example implementation, the base defines a plurality of fenestrations and further comprises a plurality of pedestals.

In an example implementation, the device further includes a quick lock/release pin configured to engage with the shaft to facilitate adjustment of the length of the shaft. In an example implementation, the device further includes a quick lock/release assembly including a pin, a push button, and a pivot coupled to both the pin and the push button to facilitate adjustment of the length of the shaft.

In an example implementation, the body is sized and shaped to contour to the abdomen of a patient. In an example implementation, at least a portion of the body has a curved periphery.

In another aspect, a device is provided for drainage of contents of an ostomy pouch. The device comprises: a base; an extendible shaft configured to provide adjustment of a length of the shaft, the extendible shaft having a lower end coupled to the base and having an upper end; a body configured to receive the ostomy pouch while the pouch is attached to a patient, the body having an upper end defining a body inlet configured to receive the ostomy pouch, the body having a lower end defining a body outlet configured to direct the contents of the ostomy pouch out of the body; a pivoting mechanism pivotally coupling the lower end of body to the upper end of the extendible shaft, the pivoting mechanism engaging the body between the body inlet and the body outlet to provide adjustment of an angle between the body and the extendible shaft; and a chute coupled to the body outlet and configured to receive the contents of the ostomy pouch from the body while the pouch is attached to the patient, the chute having an upper end coupled to the outlet end of the body, the upper end of the chute defining a chute inlet configured to direct the contents of the ostomy pouch into the chute, and having a lower end defining a chute outlet configured to direct the contents out of the chute while the pouch is attached to the patient.

In another aspect, a device is provided for drainage of contents of an ostomy pouch. In an example embodiment, the device comprises two components: a stand or Lower component I (including a base and a shaft); and a conduit or upper component II (including a body and a chute). The two components are coupled together with a pivoting mechanism. Providing further details, the device comprises: a base; an extendible shaft configured to provide adjustment of a length of the shaft, the extendible shaft having a lower end coupled to the base and having an upper end; a conduit with a body configured to receive the ostomy pouch while the pouch is attached to a mobile patient in an upright position, the body having an upper end defining a body inlet configured to receive the ostomy pouch, the body having a lower end defining a body outlet configured to direct the contents of the ostomy pouch out of the body; a chute coupled to the body outlet and configured to receive the contents of the ostomy pouch from the body and to direct the contents into the receptacle while the pouch is attached to the mobile patient, the chute having an upper end coupled to the outlet end of the body, the upper end of the chute defining a chute inlet configured to direct the contents of the ostomy pouch into the chute, and having a lower end defining a chute outlet configured to direct the contents out of the chute and into the receptacle while the pouch is attached to the mobile patient; and a pivoting mechanism pivotally coupling the lower end of body to the upper end of the extendible shaft, the pivoting mechanism engaging the body between the body inlet and the body outlet to provide adjustment of an angle between the body and the extendible shaft.

In another aspect, a device is provided for drainage of contents of an ostomy pouch. The device includes: a base; an extendible shaft configured to provide adjustment of a length of the shaft, the extendible shaft having a lower end coupled to the base and having an upper end; a conduit with a body configured to receive the ostomy pouch while the pouch is attached to a patient, the body having an upper end defining a body inlet configured to receive the ostomy pouch, the body having a lower end defining a body outlet configured to direct the contents of the ostomy pouch out of the body; a chute coupled to the body outlet and configured to receive the contents of the ostomy pouch from the body while the pouch is attached to the patient, the chute having an upper end coupled to the outlet end of the body, the upper end of the chute defining a chute inlet configured to direct the contents of the ostomy pouch into the chute, and having a lower end defining a chute outlet configured to direct the contents out of the chute while the pouch is attached to the patient; and a pivoting mechanism pivotally coupling the lower end of body to the upper end of the extendible shaft, the pivoting mechanism engaging the body between the body inlet and the body outlet to provide adjustment of an angle between the body and the extendible shaft.

DETAILED DESCRIPTION

Generally, the present disclosure provides a device for the sanitary drainage of the contents of an ostomy pouch into a waste receptacle (e.g., a toilet). The device includes a base; an extendible shaft coupled to the base; a body that receives the ostomy pouch while it is attached to a patient and directs the contents of the pouch into a chute; a pivoting mechanism that couples the body to the shaft to adjust the angle there between; and a chute coupled to the body that directs the contents of the ostomy pouch into the waste receptacle. The device and the adjustability that it provides offers patients, particularly mobile patients, the ability to empty their ostomy pouches into a waste receptacle, such as a toilet, while in a standing position.

Further, the present disclosure generally provides a durable, reusable portable drainage device for human biological waste disposal. The device is designed for mobile ostomy patients to sanitarily and ergonomically drain their ostomy pouch contents into a waste receptacle, such as a conventional toilet or similar fixture from a comfortable standing position. The device does not require attachment to a waste receptacle (e.g. toilet).

Embodiments of a device as described herein include two components. The first component, Component I, comprises a stand having a base, and an extendible shaft coupled to the base. The second component, Component II, comprises a body that receives an ostomy pouch while it is attached to a patient and directs the contents of the pouch into a chute; a pivoting mechanism that couples the body to the shaft of the stand and adjusts the angle therebetween; and a chute coupled to the body that directs the contents of the ostomy pouch into a waste disposer or waste receptacle. The device components and the adjustability that they provide, including the shaft length adjustment and the body angulation, offers patients, particularly mobile patients, the ability to empty their ostomy pouches into a waste receptacle, such as a toilet, while in a standing position. As described herein, the device provides for a relatively easy assembling and disassembling of the device components, collapsing of the extendible shaft length, and folding of the shaft over the base to facilitate portability.

Herein described is a durable reusable drainage device for human biological waste disposal, and designed for mobile patients having an ostomy to sanitarily and ergonomically drain their ostomy pouch waste contents into a receptacle, such as a conventional toilet or similar receptacle/fixture from a comfortable standing position.

Common Sanitary Practices for Individuals without an Ostomy

Current civil sanitary norms for intact individuals (i.e. that do not have an ostomy) entail discarding their waste in a receptacle or waste disposer, such as a toilet, connected to a confined environment such as a sewer system where available. Advanced sanitation and hygiene have improved public health, peoples' lives and reduced environmental hazards to humans.

Toilets, as human waste receptacles, have been in use for several centuries as fixtures to dispose of human waste in a sanitary fashion. For intact individuals using a toilet for waste disposal, the process is usually quick, easy, convenient, hygienic and sanitary. Most conventional (e.g., Western-style) toilets are constructed as fixtures of varying heights and configurations, installed in architecturally confined spaces. Toilet bowls have a trap with a "water seal" to avoid backup of sewer gases, and to dampen stool odor, where the top of the water seal is termed the waterline. For humans, to dispose of fecal waste while standing up is an abnormal process. Typically, people sit on a toilet or squat to push their lower body parts away from the waste disposal path. Urinals, a variant of toilets for urination usually not requiring a water seal, are typically installed in public washrooms at varying heights, allowing men to urinate while standing up. Portable toilets are designed for temporary installation at outdoor locations, such as construction sites or campgrounds, to cater to mobile individuals' needs.

Individuals with impaired mobility may use accessory devices such as a toilet seat "riser" (e.g., a few inches high) with or without armrests, or commodes. Motorized adjustable-height toilets are available in select locations in the world; and, typically, are installed in places where permanently disabled individuals live. Such toilets require costly bathroom reconfiguration, changes in plumbing and electrical connections to operate the height control switch.

Ostomy Patients

After intestinal or urinary diversion surgery, a patient is left with an artificial abdominal wall opening that allows biological waste (stool or urine) to flow out of the patient's body. This opening is referred to as "ostomy" or "stoma". Following an ostomy surgery, the patient requires a pouch or bag for collection and temporary storage of their waste until drained and discarded.

Depending on the condition of the patient and the nature of the disease, the created ostomy would either be temporary (surgically reversed after a few months) or permanent (such as an urostomy).

Consequences of Ostomy Surgery

Several hygienic and sanitary issues result from intestinal or urinary diversion surgery because of the multistep, and awkward ways required by the patient, or their assistant, for biological waste disposal. Embarrassment, social isolation, a need for physical assistance, living space re-configuration, and added financial burden associated with ostomies, pose challenges for many such patients particularly those with additional disabilities.

After an ostomy surgery, patients require a pouch to be attached to the stoma site to temporarily collect the bodily waste (stool, intestinal gas, or urine) until drained. Several reputable manufacturers produce a variety of ostomy pouches. Pouches are constructed of one or two pieces. For efficiency and financial reasons, most pouches are drainable; i.e., they are not to be discarded after a single use. Periodic emptying of the pouch is required when it becomes one-third to half-full, and before engaging in strenuous or intimate physical activities. The frequency of drainage depends on the type of ostomy and liquidity of the waste, and can reach up to 10 times or more per day.

The back of each pouch has a flange (skin barrier) that sticks to the patient's abdominal wall around the ostomy to protect the skin from harmful effects of the waste, and to secure the pouch in place. A small pre-fabricated hole in the flange needs to be tailor-cut prior to pouch application to ensure that it fits well around the ostomy contour, allowing stool, flatus, or urine to pass into the pouch without leakage. Some pouches have a filter to trap odor. Patients usually have to try several pouches before selecting a type that best suits their needs.

After emptying fecal contents of an ileostomy or colostomy pouch, its open lower end needs to be gently flushed with water, using a jug with a nozzle, a squeeze-spraying bottle, or other appropriate means. The open lower end of the pouch is then dried (e.g., with toilet paper) before closing it. Some stool collection pouches may have an inner liner (e.g., a disposable internal bag) that is to be removed and discarded along with its waste contents, either in a receptacle (e.g., a toilet, or other fixture), or as garbage whilst the external ostomy pouch is left attached.

Patients with urostomy are advised to diligently empty their pouch while awake. Before retiring to bed, in order to minimize sleep interruptions, the patient needs to connect a tube to the lower end of the urostomy pouch to allow for gravitational flow of urine into a larger storage container, or a large urine collection bag placed at a lower level such as the bedside floor. Upon awaking, the patient would empty the container or the bag in a receptacle (e.g., toilet). In urostomy patients, backflow, stagnation and impediment to gravitational outward urine flow can cause serious urinary tract and kidney infections, with potential loss of renal function. To avoid deleterious back-pressure effects to the urinary system, the patient needs to diligently empty the urostomy pouch; avoid sleeping with it full of urine; and, avoid kinking or blockage of the tubing or over-accumulation of urine in the storage container or bag. To decontaminate a urinary storage device before reuse, it needs to be flushed with water and/or vinegar and left to dry.

Common Sanitary Practices for Individuals with an Ostomy

While in hospital shortly after ostomy surgery, a handheld container is used to help a bedridden patient empty biological waste accumulated in their ostomy pouch. A kidney (bean)-shaped container is usually snugly pressed against the abdominal wall below the ostomy pouch to collect the waste and avoid leakage. The container is then emptied in a receptacle (e.g., toilet), and the container is either cleaned (if reusable), or discarded as garbage (if disposable).

Upon returning back to the community, the patient has to adopt one or more of several available resources, and time-consuming options to discard the ostomy pouch waste. The options include: (1) emptying an ostomy pouch directly into a receptacle (e.g., conventional Western-style toilet); (2) using one or more accessory devices to help drain the pouch contents into a waste disposer (e.g., toilet) or other receptacle, where these devices may be durable and reusable, and with or without some disposable components, or fully disposable devices; (3) using flushing devices to wash out fecal contents of an ostomy pouch into a receptacle (e.g., toilet), where some are used with the pouch still attached to a patient, or otherwise detached from the patient; (4) using a suction device to drain an attached ostomy pouch into a reservoir to be emptied later; and, (5) changing the ostomy pouch every 3 to 5 days on average, or earlier if necessary, where the used pouch is discarded as garbage along with any residual waste.

Currently existing methods for draining ostomy pouches can be repugnant, cumbersome, inconvenient, unhygienic and unsanitary; and can be fraught with possible soiling and contamination by human waste, and any contained pathogens. Soiling may impact the ostomy patient, individuals in the vicinity, subsequent users of the same toilet facility, and the environment at large when a pouch or its contents are discarded as garbage.

Draining an Ostomy Pouch Directly into a Receptacle

Receptacle (e.g., toilet) fixtures are variably configured and installed in different ways across communities. After discharge from a hospital, an ostomy patient is faced with the problem of how to best empty an ostomy pouch using their existing home toilet facility. For humans to dispose of fecal waste while standing up is an abnormal process. Typically, individuals sit down on a fixed-height toilet to dispose of their waste. Sitting or squatting positions push the individual's lower body parts away from the waste disposal path to avoid potential soiling and contamination.

In order to drain a stool-containing pouch, mobile ostomy patients may intuitively empty the waste directly into, for example, a conventional (Western-style, fixed-height) toilet. To do so, the patient would have to assume one of several awkward positions by either sitting far back on the toilet seat, sitting in reverse facing a toilet flusher, straddling the toilet, or kneeling next to the toilet. The patient (or an assistant) would then open the drainable lower end of the pouch to allow waste to empty into the toilet bowl from a distance of several inches high above the waterline. This distance to the waterline is even longer if the patient is seated on a higher toilet seat or riser. In case of a squatting toilet or latrine, drained waste would have to be aimed carefully at their opening on the floor level. To empty an ileostomy or colostomy pouch, its attached or integrated closure mechanism is opened to drain accumulated stool.

Similarly, with a urostomy pouch, the tap-like valve at its lower end is opened to drain contained urine.

Urinals, as alternative urine disposal fixtures, are generally installed in public restrooms at a higher level than those of conventional toilets. In such cases, the shorter drainage distance between an ostomy pouch and the bottom of the urinal may present a more sanitary and convenient way for patients with urostomy to empty their pouch from a standing position with less risk of soiling. However, access to urinals for those urostomy patients is limited to certain locations and hours of availability. Only in select locations, a patient with an ostomy may drain the pouch while standing next to a motorized, height-adjustable, toilet bowl installed in washrooms designated for disabled individuals in their equipped residence or in some public washrooms for special needs individuals in Japan having large self-flushing sinks fixed at a higher level than conventional toilets.

Disadvantages and Limitations of Directly Emptying Ostomy Pouch Contents into a Receptacle (e.g., Conventional Waste Disposer, Such as Toilet)

Disadvantages and limitations of directly emptying ostomy pouch contents into a conventional waste receptacle (e.g. Western-style fixed-height toilet) include: (1) because of the distance to a receptacle waterline, when emptying an ostomy pouch directly into it, there is potential for soiling and microbial contamination from trickling, spilling, or splashing of waste, or the contaminated water seal splashback; (2) soiling and contamination are hazardous, not only for a patient, but also for individuals in the vicinity (such as an assistant), or for those who may subsequently use the same toilet facility; (3) attempting to freely drain a pouch fecal contents from a standing position, into a receptacle, is not recommended since the physical gap between the ostomy pouch and the receptacle waterline becomes significantly longer, thus increasing potential soiling and contamination along the path of waste disposal, including the patient's body parts below the ostomy level; (4) a patient would need to assume an awkward and sometimes painful position, particularly shortly after abdominal surgery, when emptying an attached pouch directly in a conventional toilet; (5) and, overweight, elderly and patients with additional disabilities, especially those with joints problems, may encounter increased difficulty, or even impossibility, when attempting to assume such awkward or painful positions particularly after recent surgery; and (6) urinals are installed at various levels, usually higher than those of conventional toilets, and may present an easier and more sanitary way for patients to stand and empty their urostomy bags because of the shorter drainage distance; however, access to urinals may be limited for some patients, and to certain locations (e.g., public restrooms).

Final Steps of Waste and Ostomy Pouch Disposal

Although costly, ileostomy, colostomy, or urostomy pouches usually need replacement, every 3 to 5 days on average, to avoid potential deleterious effects to the underlying skin. The used pouch is then discarded as garbage with any residual contents.

Use of Accessory Drainage Devices to Empty an Ostomy Pouch

Collected biological waste in an ostomy pouch may be emptied into a durable and/or reusable accessory device, or into a waste collection bag, a container, or other disposable accessory device while the patient is either in a standing position or sitting position.

When a container is used, it is typically held close to a patient's ostomy pouch; alternatively, it may be attached to a front part of the receptacle (e.g., toilet's rim) at time of drainage, the filled receptacle then being emptied (e.g., in a waste disposer, toilet), or discarded as garbage.

Alternatively, some drainage devices include collecting systems with fully or partly disposable receptacles, where some of the receptacles have securing means for holding the bodily waste material-receiving chamber in position relative to the ostomy. Some disposable receptacles are made of biodegradable material to be toilet-flushable.

Disadvantages and Limitations of Fully or Partly Disposable Drainage Devices for Ostomy Pouch Drainage Include:

(1) Emptying an ostomy pouch using accessory disposable bags, containers, receptacles and frame-like platforms may require their subsequent discarding as garbage, adding to increasing problems of non-degradable environmental and biological waste; (2) use of biodegradable bags for collecting waste that are subsequently dropped in a toilet carry a risk of plugging sewage/drainage systems if the bag fails to degrade or the contents are solid enough; (3) processes used may be cumbersome and unsanitary; (4) disposable receptacles may require timely supplies and storage space; (5) cost for disposable supplies may be significant, especially for disabled individuals with potentially limited funds and earning ability; (6) diarrhea may increase frequency of waste disposal at an increased cost; (7) financial burden may be higher for patients with a permanent ostomy; (8) use of a plastic disposable device adds to increasing problems of non-degradable environmental waste; (9) the higher the number of intermediate steps required for disposal of biological waste, the higher the risk of contamination compared to a more direct disposal technique.

Flushing Fecal Contents of the Ostomy Pouch Directly in a Toilet

A patient may use a device that provides a water stream to directly flush a drainable colostomy or ileostomy pouch's fecal contents into a receptacle (e.g., toilet) using one of several accessory devices. The water stream would either be directed top-down through an opening constructed in an upper part of the pouch, or bottom-up through the pouch's drainable lower end.

Disadvantages and Limitations of Ostomy Pouch Flushing Devices Include:

(1) Because of potential splashing, flushing of a stool-containing ostomy pouch directly in a toilet using a water stream can be cumbersome, potentially messy, unhygienic and unsanitary; (2) flushing an ostomy pouch with pressurized water flow may separate an ostomy pouch skin barrier from its attachment site around a stoma, resulting in waste leakage and inflammation of the peri-stomal skin requiring a pouch change and added cost; (3) an accessory device and a source of running water are required; (4) plumbing is required to connect a flushing device to a bathroom fixture or a water source, as well as a means of controlling water pressure, where water temperature control may or may not be available; and, (5) such devices would not be portable if permanently attached to a toilet fixture or a water supply.

Using a Suction Device to Drain an Ostomy Pouch

By using such devices, fecal contents of an ostomy pouch can be suctioned into a container. It would require a specially designed ostomy pouch for collection of the fecal drainage from colostomies and ileostomies. The ostomy pouch would be connected by tubes to the container, which in turn is connected via tubes to a vacuum device. Fecal waste collected in the container is subsequently discarded.

Disadvantages and Limitations of Emptying the Stoma Pouch Using Suction Include:

(1) frequent suction or inadvertent high power suction of an ostomy pouch may result in collapse of the pouch, herniation of the stoma and/or body structures around it, resulting a parastomal hernia; (2) a suction device may become contaminated and may act as a potential source of pathogenic microbial spread to others; and (3) handling accumulated waste in the container carries a risk of spillage, in addition to environmental hazards if the waste contents are discarded as garbage.

A Novel Device for Sanitary Drainage of an Ostomy Pouch

When draining contents of an ostomy pouch directly into a receptacle, such as a toilet, there is a potential problem of soiling and contamination by human waste and any contained microbes. The long physical gap between the ostomy pouch and any receiving receptacle or receptacle's waterline may result in inadvertent trickling, spillage, splashing or spattering of biological waste.

As such, the device for sanitary drainage of an ostomy pouch of an embodiment as described herein is designed to at least provide a portable reusable device providing one or more of the following characteristics: (I) that may be used as an accessory sanitary apparatus allowing a mobile patient to easily, and sanitarily drain an ostomy pouch waste into any receptacle (e.g., toilet, other fixture container, etc.) from a comfortable standing position; (II) that may have a simple and ergonomic design; (III) that offers height and angle adjustability of the device to bring it up to an ostomy site; (IV) having a chute that may have an extendible length, and that may have a fixed angle between upper and lower ends of the chute to bring a discharging outlet of the chute as close as possible to the receptacle's waterline; (V) where the height and angle adjustability features may bridge the long physical gap between an ostomy pouch and receptacle; (VI) having a body configured to receive an ostomy pouch while it is attached to a patient, the body conforming to the patient's abdominal wall contour; (VII) the body defining a body inlet that further defined a rim around the periphery of the body inlet (e.g., splash guard), the rim being configured to obstruct potential splash-back of contents from an ostomy pouch during drainage; (VIII) that may be durable, reusable, and cost effective; (IX) that is unattached from a receptacle or water supply; and, (X) that may be lightweight, and easily assembled and dis-assembled, to be portable for transportation and travel.

In an example as described herein, there is provided a device for sanitary drainage of an ostomy pouch that allows patients, particularly mobile patients, with an ostomy to easily and sanitarily drain their ostomy pouch in a convenient, ergonomic and hygienic way, from a comfortable standing position into any receptacle or waste disposer, such as a toilet.

In another example as described herein, there is provided a device that is an accessory sanitary drainage device that bridges the long physical gap between an ostomy pouch and any receiving receptacle, such as a toilet waterline.

In another example as described herein, there is provided a device for sanitary drainage of an ostomy pouch having a simple design that allows a patient, particularly a mobile patient, to easily drain the contents of their ostomy pouch through the device into any nearby sanitation fixture, such as a conventional Western-style toilet, squatting toilet, or other equivalent receptacle or waste disposer, such as a portable toilet (e.g. a porta potty) or latrine.

In an example of the device as described herein, the device is a simple, portable, durable, lightweight, reusable device with a conduit comprised of a funnel-shaped body coupled to a tubular, angled chute. For operation of the device, the body is pivotally coupled via a pivoting mechanism to the upper end of an extendible shaft, the shaft being coupled at its lower end to a stable base. The device includes two components (lower component I and upper component II) that are coupled together. The device may be constructed out of durable, lightweight, waterproof, easily washable, sturdy, and rustproof materials.

In an example as described herein, there is provided a device for sanitary drainage of an ostomy pouch that is lightweight, and easily assembled and disassembled making it portable for transportation and travel. In another example as described herein, there is provided a device for sanitary drainage of an ostomy pouch made of components that are easily assembled and setup for use. In another example as described herein, there is provided a device that is easily dis-assembled, collapsed and folded up for transportation. In another example, there is provided a device that would not require to be attached to any waste disposer or receptacle (e.g. toilet) or to a water source.

In an example as described herein, there is provided a device for sanitary drainage of an ostomy pouch comprising a stand having an extendible shaft, configured to provide adjustment of a length/height of the shaft, coupled at its lower end to a base (for example, with hinged plates), and coupled at its upper end to a body via a pivoting mechanism that provides adjustment of an angle between the body and the extendible shaft.

In an example described herein, there is provided a device for sanitary drainage of an ostomy pouch contents having a conduit body configured to receive an ostomy pouch while it is attached to a patient, the body defining a body inlet and having a curved contour to conform to the patient's abdomen, and to allow the body inlet to be brought up to snugly fit against the patient's abdomen just below the ostomy pouch, whether it is on the right or the left side of the patient.

In an example as described herein, there is provided a device for sanitary drainage of an ostomy pouch having a body configured to receive an ostomy pouch while it is attached to a patient, the body defining a body inlet that further defines a rim around the periphery of the body inlet (e.g., splash guard), the rim being configured to obstruct potential splash-back of contents from an ostomy pouch during drainage.

In an example as described herein, there is provided a device for sanitary drainage of an ostomy pouch having an extendible chute, the chute having a fixed angle between its upper and lower ends so that the chute can be angled and extended down as close as possible to a receptacle, such as a toilet and its waterline, to prevent "splash-back".

In an example as described herein, there is provided a device for sanitary drainage of an ostomy pouch that is durable and cost effective.

In an example as described herein, there is provided a device for sanitary drainage of an ostomy pouch that is reusable; for example, where the interior of the device can be flushed after use with water from an available water source.

Potential benefits for a patient using a device for sanitary drainage of an ostomy pouch, as described herein, with a receptacle such as a toilet include one or more of the following: (I) being able to place the device at a convenient location next to a receptacle facilitates ostomy pouch drainage and reduces potential contamination; (II) being able to easily bring the device's body up and fit it against the patient's abdominal contour at an ostomy's level, whether the stoma is constructed on the right side (usually ileostomy or urostomy) or on the left side (usually a colostomy); (III) being able to use the device in a standing position for drainage of the ostomy pouch, obviating a need for the patient to assume an awkward or restrictive position when draining their pouch in a receptacle, such as a conventional fixed height toilet; (IV) using the device in a standing position, which is ergonomically advantageous for all patients, particularly postoperative overweight and elderly patients, or those with joints problems; (V) using the device in a standing position improves visibility and access to an ostomy pouch; (VI) being able to ergonomically operate the device, which facilitates drainage of, for example, an urostomy pouch and encourages those patients to frequently empty their pouches, thus decreasing the potential for microbial growth and urinary infections; (VII) being able to ergonomically operate the device, which reduces a patient's reliance on assistance and offers the patient independence, privacy and confidence; (VIII) being able to ergonomically operate the device, which would save a patient time when draining the ostomy pouch; (IX) being able to ergonomically operate the device, which would reflect positively on the patient's overall quality of life; and (X) the device being durable and reusable, which may reduce any financial burden associated with use of disposable containers or devices, particularly for patients with permanent ostomy.

Positive environmental impacts of a device for sanitary drainage of an ostomy pouch, as described herein, include one or more of the following: (I) flushing the contents of the device into a receptacle, such as a toilet, after its use and subsequent flushing of the toilet would drain biological waste into a confined environment, ideally in a sewer system; (II) using the device may reduce potential contamination that could otherwise result from discarding waste, and any associated pathogens, as garbage or into an open environment (such as a landfill); (III) before discarding an ostomy pouch, using the device to empty the waste contents into a receptacle, reduces potential contamination of an open environment where the pouch may end up as garbage; (IV) repeated use of the device may reduce the inorganic waste load, and the need for production of disposable ostomy internal lining bags, accessory collection receptacles and plastic garbage bags.

With reference to FIGS. 01 to 21, in accordance with embodiments of the present disclosure, there is depicted device 101 and device 201. Each example implementation includes two components; an upper component (Component II, the conduit; including body and chute) and a lower component (Component I, the stand). Component IIa for device 101 is different from Component IIb for device 201 wherein each has a distinct configuration of the funnel-shaped body (no. 111 and 211) and a corresponding detachable lid to engage and cover the corresponding body.

With reference to FIGS. 01 to 21, in respect of device 101 and device 201, there are depicted embodiments of the lower Component I (the stand). In an embodiment, the stand (no. 161) has a base (no. 14); an extendible (e.g., adjustable-height) shaft (no. 151) with at least two telescoping sleeves (no. 5 and 29); a lever (no. 3) to support component II (the conduit) when the device is setup for use; two hinged plates, one plate attached to the shaft inner sleeve lower front end (no. 12), one attached to the base upper surface (no. 13) with a hinge there between, to allow folding up of the base over the shaft; a longitudinally moveable bracket (no. 8) to anchor the vertically positioned shaft down into the base when the device is in use; and a horizontally slidable lock (no. 31) to immobilize the longitudinally moveable bracket, after pulling it up to disengage the bracket from the base and before folding the base up onto the shaft for transportation.

Also depicted is an alternative embodiment of a quick lock/release assembly to adjust the length of the extendible shaft and to fix the external and internal sleeves at a desired position relative to each other for height adjustment of the shaft in lieu of using commercially available quick lock/release pins.

As depicted in the Figures, there is depicted two devices: device 101 and device 201. Each device comprises two components: a lower component I (the stand) and an upper component II (the conduit). Both components, the stand and the conduit, are coupled together by way of a pivoting mechanism.

Each of device 101 and device 201 comprise a body that is generally funnel-shaped (no. 21 and 35) and a corresponding lid (no. 16 and 33) configured to engage an upper end of the body defining a body inlet. Each body is coupled to a tubular, angled chute for drainage of contents of an ostomy pouch (not shown), for example, into a receptacle or waste disposer (e.g., a toilet, etc.; not shown).

With reference to the Figures, in an embodiment the stand (no. 161) comprises a semicircular base (no. 14) with a plurality of fenestrations (no. 91) and a plurality of pedestals (no. 15); an extendible shaft (no. 151) with an external sleeve (no. 5) and an internal sleeve (no. 29) configured to couple together at a plurality of adjoining engagement points (no. 6 and 30) to provide adjustment of a length/height of the shaft; a shaft internal sleeve having a closed upper end and an open lower end coupled to the base (no. 181); a plate attached to the internal sleeve lower front end (no. 12) and the second plate attached to the base upper surface (no. 13) with a hinge there between allowing the shaft to be vertically positioned above the base when in use and for the base to fold up over the shaft for transportation; a shaft slidable external sleeve (no. 5) having an open lower end, and a closed external sleeve upper end (no. 20) between two upward projecting parallel lateral sidewalls (no. 1) extending on both sides of the external sleeve above its closed upper end, the sidewalls ending with pointed apices to support the undersurface of the body (no. 21); a longitudinally moveable bracket (no. 8) secured in place by a plurality of ring-like tubular sockets attached to the back of the external sleeve (no. 9), the bracket having an upper end slightly curved back to facilitate gripping, and a lower end for engaging and anchoring the external sleeve into a slot at the base (no. 10) to steady the shaft in a vertical position when the device is setup for use; a horizontally slidable lock assembly (no. 31) situated over the closed upper end of the external sleeve between the sidewalls, whereby the lock upon deployment (when pushed back beyond the rear of the external sleeve top) protrudes to engage and immobilize the elevated longitudinally moveable bracket upper end, allowing the base to freely fold up over the shaft for transportation; a lever made of two rods (no. 3) joined at their front ends allowing the lever to support the body at a chosen angle when in use; the lever rear ends defining vertically oriented circular holes at each side to couple to the upper end of the external sleeve by way of, for example, a commercially available wingnut (no. 4); the wingnut when deployed engages the lever rear circular ends and the second from the top opposing holes in the shaft external sleeve sidewalls (no. 2) to maintain the lever at a desired angle; and two flat brackets with opposing holes (no. 11) attached vertically at a right angle to the base front upper surface (no. 11) in parallel such that an appropriate distance between the brackets would accommodate the shaft when the base is folded up over the shaft for transportation.

With reference to the Figures, two embodiments are depicted of the conduit body (Component II) both configured to receive the ostomy pouch while the pouch is attached to a patient; each body (no. 21 and 35) having a wider upper end defining a body inlet configured to receive the ostomy pouch; the body inlet having a rim (no. 18 and 34) to prevent splash-back of pouch contents; the body tapering into a narrower lower end (no. 22) defining a body outlet configured to direct the contents of the ostomy pouch out of the body.

The example implementations of the conduit (Component II) of device 101 and device 201, as depicted in the Figures, have two different body configurations, each meant to appropriately fit various abdominal contours: the body (Component IIa) for device 101 (no. 111), and the body (Component IIb) for device 201 (no. 211). Component IIa defines a circularly contoured body inlet, a rim, a lid, and a conical-shaped body (for patients with flat abdomen), while Component IIb defines a quasi-rectangular contoured body inlet, a rim, a lid with at least one curved side, and an appropriately sized and shaped body (to fit a patient's rounded or protruding abdominal wall).

As depicted, the remainder of the Component II elements for device 101 and device 201 are the same, including a chute coupled to the body outlet and configured to receive the contents of the ostomy pouch from the body while the pouch is attached to the patient; the chute (no. 121) having an upper end coupled to the outlet end of the body (no. 22), the upper end of the chute (no. 26) defining a chute inlet configured to direct the contents of the ostomy pouch into the chute, and having a lower end outlet (no. 27 and 26) configured to direct the contents of the ostomy pouch out of the chute and into a receptacle while the pouch is attached to the patient (e.g., configured to extend down and forward to direct contents of an ostomy pouch as close as possible into a receptacle or waste disposer).

With reference to the Figures, in an embodiment there is depicted a pivoting mechanism (141) coupling the under-surface of the body, between the body inlet and the body outlet, to the shaft upper end (apices of the external sleeve sidewalls) allowing adjustment of the angle between the conduit and the stand.

As depicted in the Figures, an example implementation of the lower Component I (the stand) includes:

(1) A base (no. 14, FIGS. 01 and 09) having a semicircular contour with a curved cut off segment at its front; and a plurality of cut-out fenestrations (no. 91, FIGS. 02 and 09) to bring its front end closer to a waste receptacle (e.g. toilet fixture) as needed, and to reduce its weight without compromising stability. The base also having a plurality of pedestals (no. 15, FIG. 01) to securely rest the base on a floor.

(2) A segment cut off the front of the base, partly defining its semicircular/lunar contour, allowing proximity of the device to fixture receptacle (e.g. toilet) when required.

(3) An extendible shaft (no. 151, FIG. 01) constructed of at least two telescopically coupled sleeves having a plurality of slots (e.g., engagement points) and configured to couple together at the plurality of engagement points to adjust the length/height of the shaft (FIG. 01, no. 6 and 30).

(4) The two telescoping sleeves, the external sleeve (no. 5, FIGS. 01 and 02) and the internal sleeve (no. 29, FIGS. 01 and 02), each having an upper and a lower end.

Figure 5:
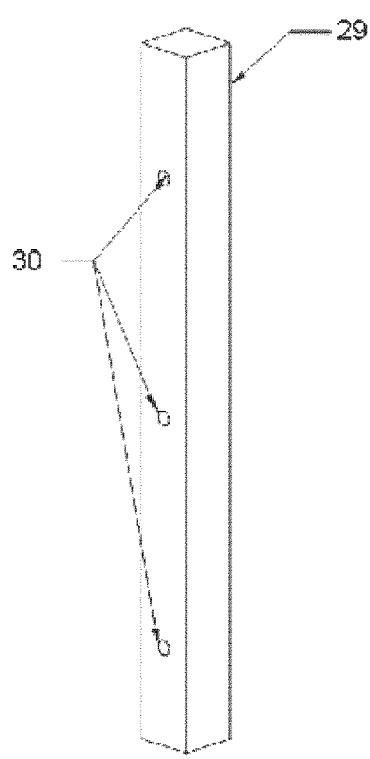
FIG. 05 depicts an angled side perspective view of an internal telescoping sleeve of the extendible shaft of device 101 and device 201 in accordance with embodiments of the present disclosure.
Figure 6:
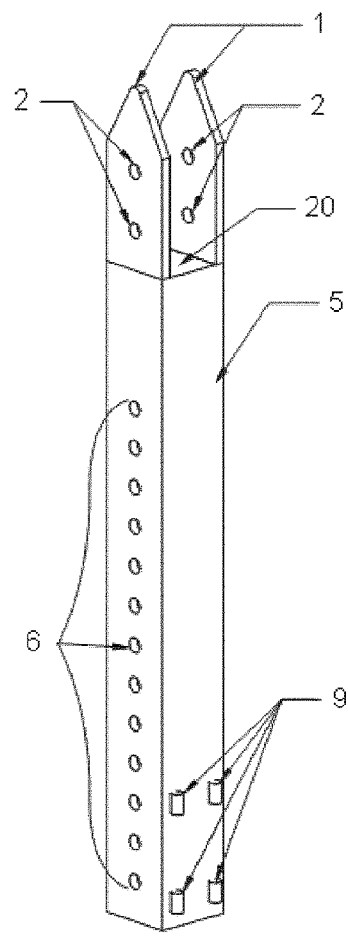
FIG. 06 depicts an angled rear perspective view of an external telescoping sleeve of the extendible shaft of device 101 and device 201 in accordance with embodiments of the present disclosure.
Figure 7:
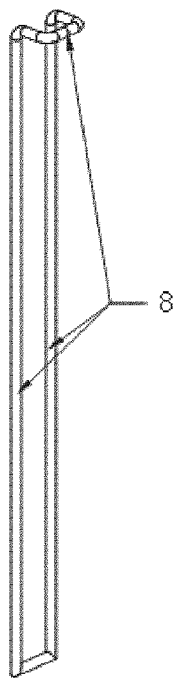
FIG. 07 depicts an angled rear perspective view of a longitudinally moveable bracket for the extendible shaft of device 101 and device 201 in accordance with embodiments of the present disclosure.
Figure 8:
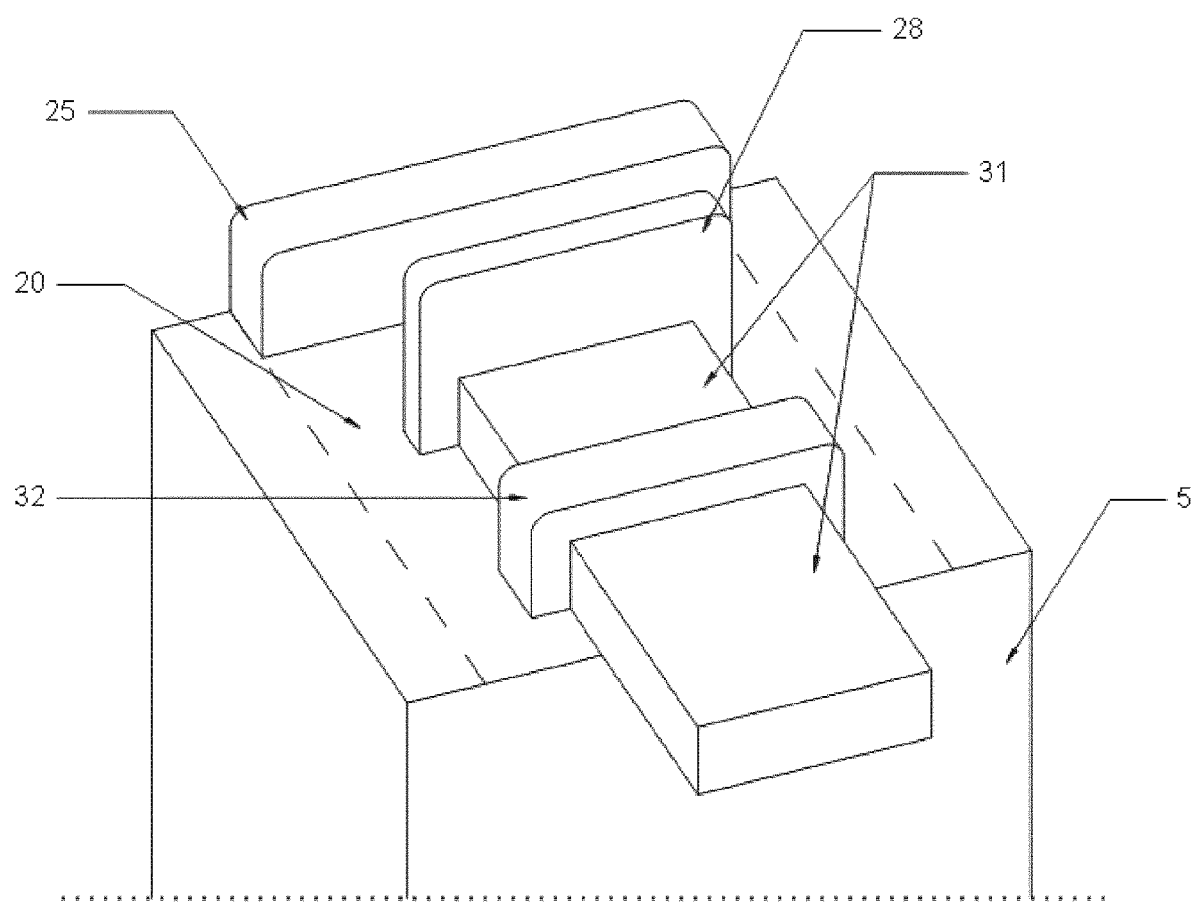
FIG. 08 depicts an enlarged angled top perspective view of a horizontally slidable lock assembly over the closed upper end of the external telescoping sleeve of device 101 and device 201, in accordance with embodiments of the present disclosure.

5) The internal and external telescoping sleeves each having a rectangular cross-sectional configuration (see no. 29, FIG. 05 and no. 5, FIG. 06).

(6) The internal telescoping sleeve having a closed top (no. 29, FIG. 05)

Figure 9:
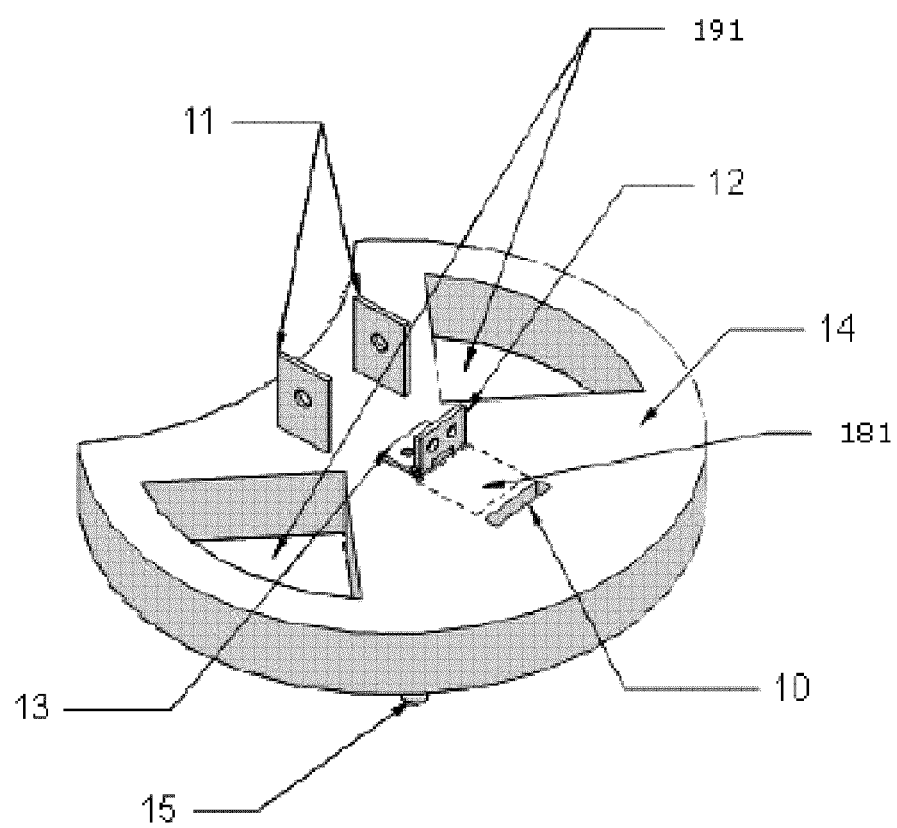
FIG. 09 depicts an angled top perspective view of a base of device 101 and device 201 in accordance with embodiments of the present disclosure.

(7) The internal telescoping sleeve lower end coupled to the base (no. 181, FIG. 09) with two hinged plates allowing the base to fold over the shaft (no. 12 and 13, FIGS. 01, 03 and 09).

(8) An external telescoping sleeve slidably fitting over the internal telescoping sleeve (no. 5, FIG. 03).

(9) The external and internal telescoping sleeves having open lower ends for cleaning purposes and for the external sleeve to slide over the internal sleeve.

(10) A gap is present between the external and internal telescoping sleeves for smooth gliding and easy adjustment of the shaft height.

(11) The external telescoping sleeve is the sliding member, or slidable element.

(12) The external telescoping sleeve having a closed upper end at a level to allow the external sleeve, when collapsed over the internal sleeve, to slidably fit just above the level of the internal sleeve closed top (no. 20, FIGS. 03 and 06 and no. 29, FIG. 05).

(13) The external telescoping sleeve having two parallel upward projecting lateral sidewalls extending up above the level of its closed upper end (no. 1 in FIGS. 03, 04 and 06).

Figure 19:
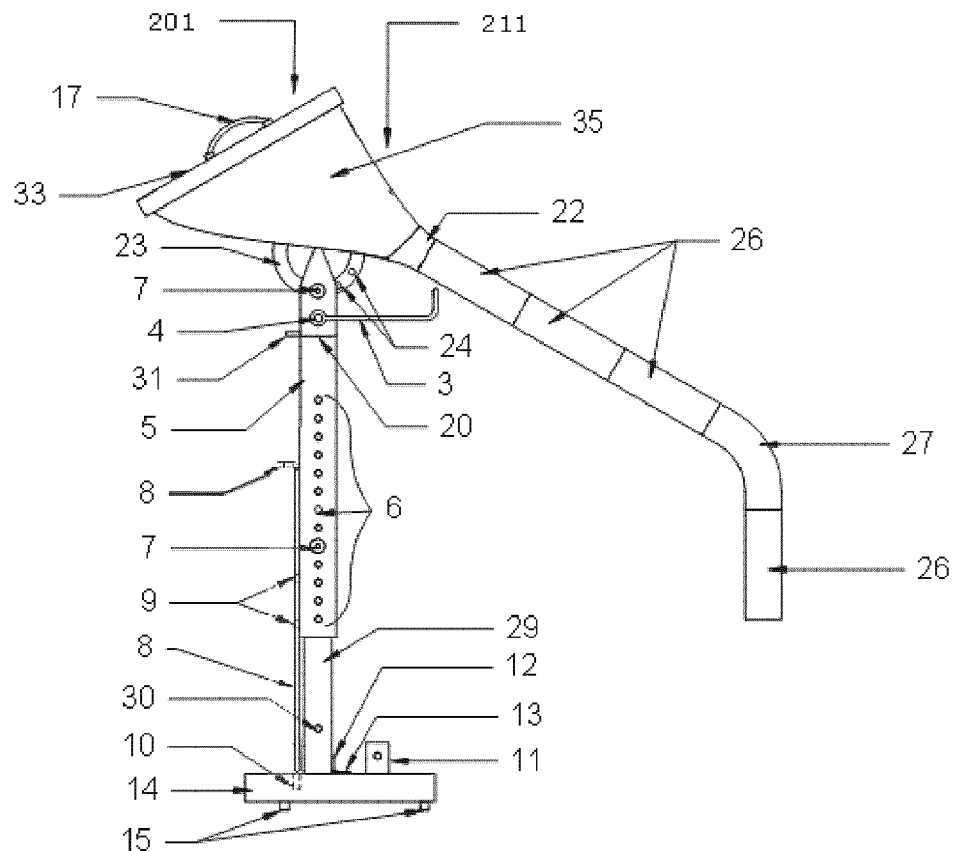
FIG. 19 depicts a side elevation view of device 201 for drainage of contents of an ostomy pouch in accordance with an embodiment of the present disclosure.

(14) Each one of the external telescoping sleeve sidewalls having a pointed tip with a half circle contour to support the under-surface of the body of each device (no. 1, FIGS. 01, 06 and 19).

(15) The external telescoping sleeve sidewalls each defining two pairs of fenestrations/holes placed linearly in a longitudinal row at an appropriate distance away from the tip of the sidewalls and apart from each other (no. 2 in FIGS. 03 and 06).

(16) A space between the sidewalls of the external telescoping sleeve of the extendible shaft engages a handle defining a fenestrated or curved perforated track, coupled to the undersurface of the body (no. 23 and 24, FIGS. 01, 10, 12 and 13).

Figure 2:
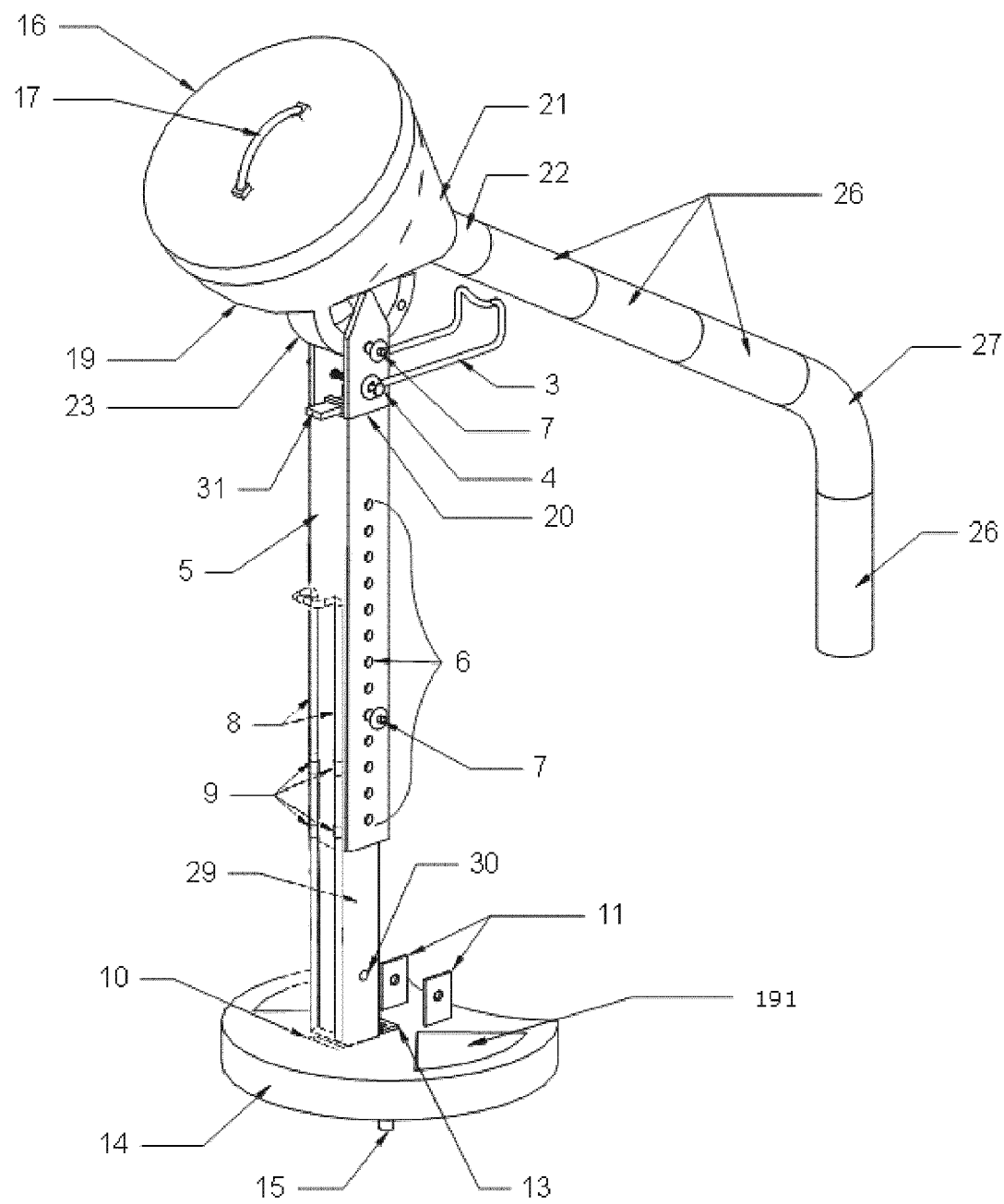
FIG. 02 depicts an angled rear perspective view of device 101 of FIG. 01.

(17) A lever configured in the form of two parallel rods with their front ends joined together in a curvilinear fashion to fit and support the undersurface of the chute, and the rear ends defining a vertically oriented circular hole on each side (no. 3, FIGS. 01 to 03).

(18) The lever circular rear end holes are coupled to the second holes from the top of the pointed upper end of the sidewalls of the external sleeve (no. 2, FIG. 03). The lever is configured to enable further adjustment of an angle between the shaft and the conduit and support the chute at a chosen angle (no. 3, FIGS. 01, 02, 18 and 19)

(19) A wingnut (or other similar fastener) to couple the back of the lever circular rear end holes with the upper end of the shaft sidewalls to facilitate adjustment of the lever angle. To securely fix the lever in a desired position, a nut is threaded over the bolt tail end on the outer side of the opposite external sleeve sidewall (no. 4, FIGS. 01 to 04, 18, and 19).

(20) A longitudinally moveable bracket having two parallel rods joined transversely together at their upper and lower ends (no. 8, FIGS. 01 to 04, 07 and 18).

(21) The longitudinally moveable bracket having an upper end slightly curved back to facilitate gripping (no. 8, FIGS. 01 to 04, 07 and 18).

(22) The longitudinally moveable bracket is secured to the back of the external telescoping sleeve with a plurality of ring-like sockets (no. 9, FIGS. 03, 04, 06 and 18) at an appropriate distance from the base allows smooth up and down sliding movements of the bracket;

(23) The longitudinally moveable bracket engages (e.g., when pushed down into) a slot in the base (no. 10, FIGS. 01, and 09) to securely anchor the shaft in a vertical position when the device is setup for use.

Figure 21:
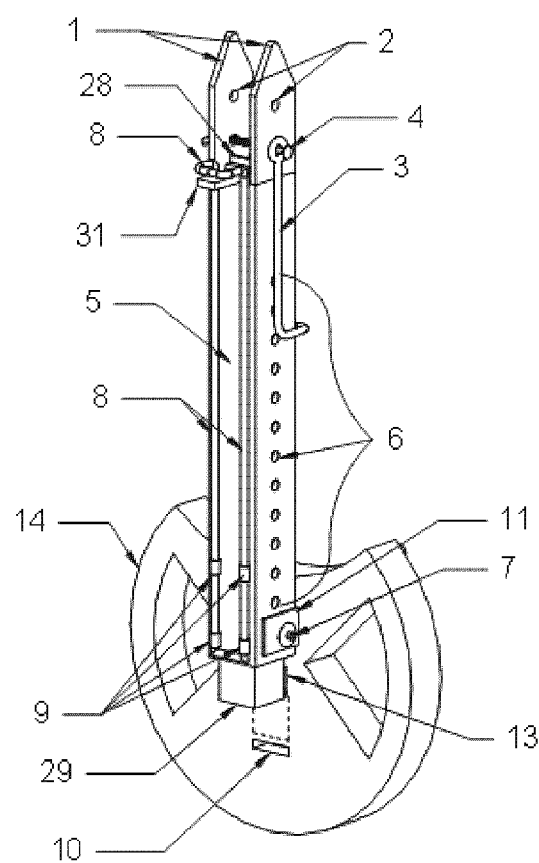
FIG. 21 depicts an angled rear perspective view of Component I (the stand) with the base folded up over the collapsed shaft ready for transportation.

(24) The longitudinally moveable bracket movement allows it to disengage from the base when preparing for changing the shaft length/height, and/or for the external sleeve to collapse down over the internal sleeve (shorten the shaft height) before folding the base up over the shaft for transportation (no 08, FIG. 21).

Figure 18:
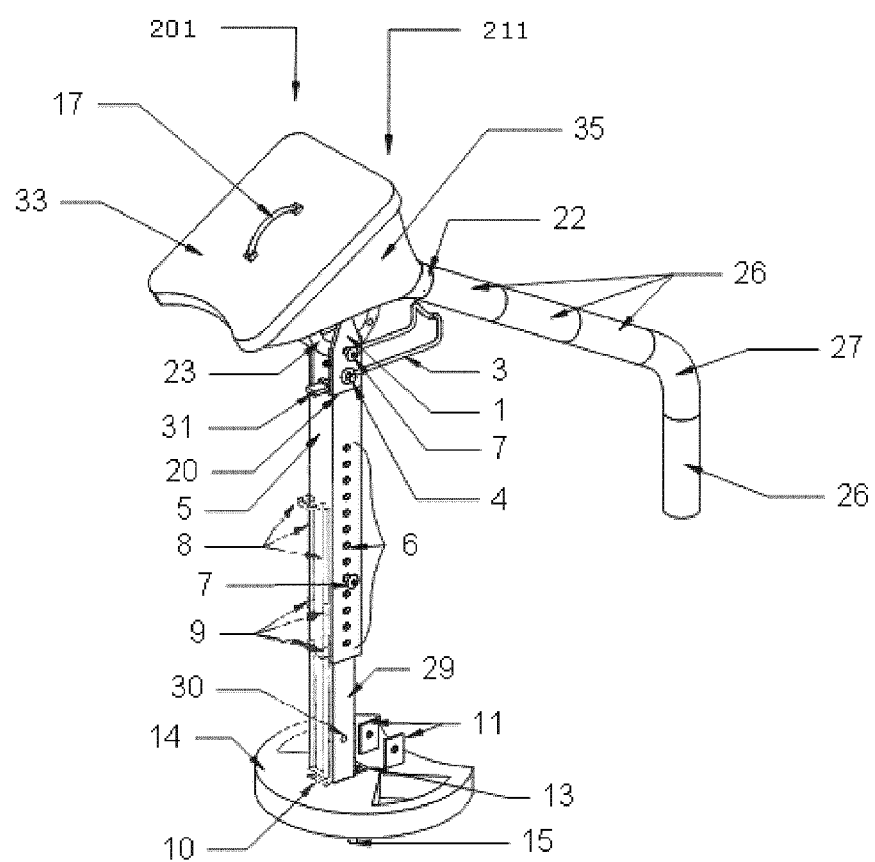
FIG. 18 depicts an angled rear perspective view of device 201 for drainage of contents of an ostomy pouch in accordance with an embodiment of the present disclosure.

(25) A configured horizontally slidable lock assembly (no. 31, FIG. 08), located above the closed upper end of the external sleeve (no. 20, FIG. 08), when deployed (pushed back beyond the rear surface of the external sleeve) engages and immobilizes the retracted longitudinally moveable bracket curved upper end, and prevents the bracket from sliding down, thus allowing the base to fold up over the shaft for transportation (no. 31, FIGS. 02, 18 and 21). The lock assembly includes a handle (no. 28, FIG. 08) to grip and facilitate the lock slidable back and forth horizontal movement; a front wall (no. 25, FIG. 08) preventing the lock from sliding forward beyond the front edge of the external sleeve closed upper end; and a bridge (no. 32, FIG. 08) controlling the lock slidable backward protrusion beyond the back edge of the external sleeve.

(26) The external and internal telescoping sleeves adjoining lateral sides define a plurality of fenestrations (holes) in a longitudinal row starting a short distance from each sleeve lower end and spaced appropriately apart (no. 6, FIGS. 01 to 03, 05, 06 and 18).

(27) A quick release/lock pin couples the opposed holes of the external and internal telescoping sleeves in a selected position relative to each other to maintain the extendible shaft length/height at a desired level (no. 06, 07 and 30, FIGS. 01, 02, 18, 19 and 21).

(28) The internal telescoping sleeve (no. 29, FIGS. 01 and 02) is coupled to the base at an off-center position (no. 181, FIG. 09) with two hinged plates. One plate attached to the internal telescoping sleeve front lower end (no. 12, FIGS. 01, 03, 09, and 19) and the second plate attached to the upper surface of the device base with a hinge there between (no. 13, FIGS. 01 to 03, 09 and 18).

(29) The hinged plates allow the extendible shaft to stand vertically at a right angle relative to the base (no. 12 and 13, FIGS. 01 and 02) when the device is intended for use (no. 8, FIG. 01) and for the base to fold over the shaft when prepared for transportation (no. 08, FIG. 21).

(30) Two parallel flat brackets, each defining an opposed hole/fenestration, are vertically fixed to an upper surface near the front end of the base, parallel to each other, and at appropriate distance from each other to allow the shaft to be housed in between them upon folding (no. 11, FIG. 09).

(31) In preparation for transportation, after the longitudinally moveable bracket is disengaged from the base, the hinged plates allow the shaft to fold over the base between its two parallel fixed brackets.

(32) A quick release pin, deployed through the holes of the two base brackets and the corresponding lowermost holes in the shaft of the external and internal sleeves (no. 6 and 30, FIG. 01) immobilizes the collapsed shaft relative to the base when the device base is folded up for transportation (no. 7 and 11, FIG. 21).

Additionally there is provided another example implementation for coupling the shaft external and internal sleeves, as described herein and depicted in FIG. 20, having a quick lock/release mechanism to adjust the shaft length/height and fix the sleeves in a desired position relative to each other (see below).

As depicted in the Figures, an example implementation of Component IIa of device 101 (the conduit no. 131, FIG. 10) includes:

(1) A detachable lid having a circular contour (no. 16, FIG. 02), a curved handle attached to the lid upper surface (no. 17, FIGS. 01 and 10) and a has a downward rim to engage and securely cover the upper end of the body inlet.

Figure 11:
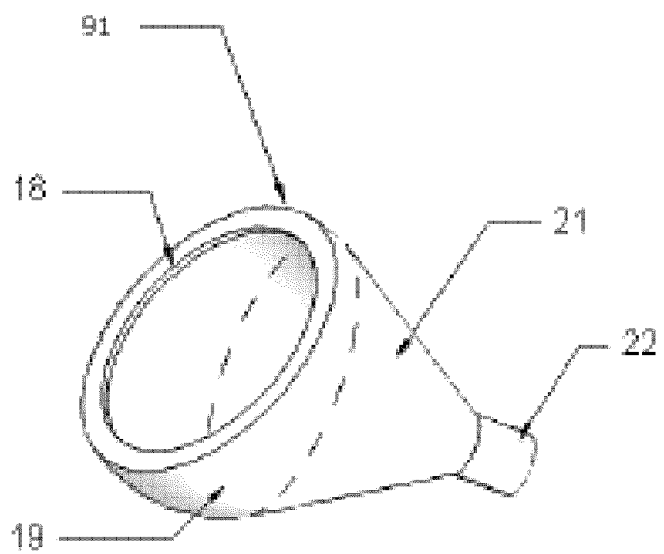
FIG. 11 depicts an angled side perspective view of the body inlet, body and body outlet for Component IIa (the conduit) of device 101.

(2) An upper end of the conduit body defining a circular body inlet (no. 91, FIG. 11).

(3) The upper end of the body further defines a rim (splash guard) around the periphery of the body inlet that extends towards the center of the body to obstruct splash-back of the contents of the ostomy pouch during drainage (no. 18, FIG. 11).

(4) A body inlet contoured to fit against a patient's abdomen and continuing as a conical lower end (no. 19 and 21, FIG. 11).

(5) The lower end of the body defines a narrower circular body outlet (no. 22, FIGS. 01 and 11).

Figure 10:
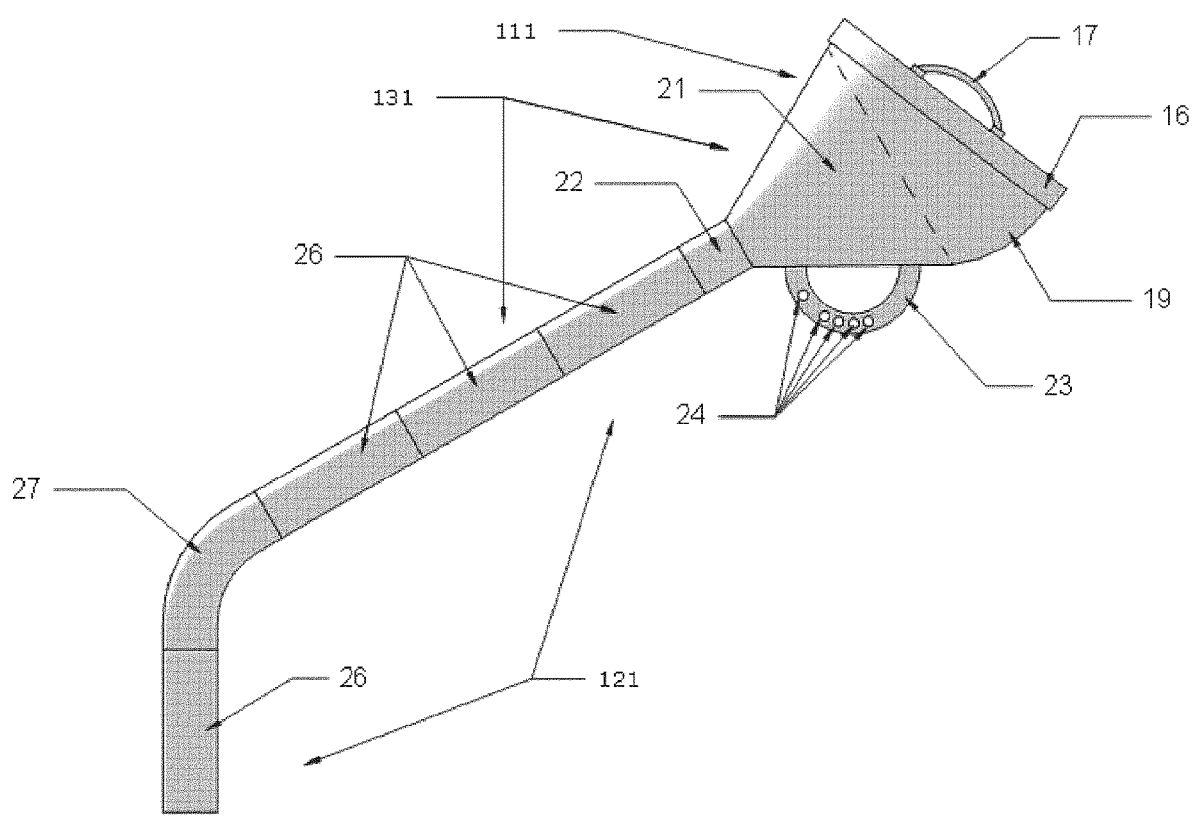
FIG. 10 depicts a side view of Component IIa (the conduit) of device 101 for drainage of contents of an ostomy pouch in accordance with an embodiment of the present disclosure.
Figure 12:
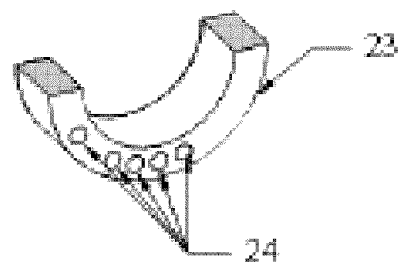
FIG. 12 depicts an angled top perspective view of a perforated curved handle of Components IIa and IIb (the conduit) for device 101 and device 201 in accordance with embodiments of the present disclosure.
Figure 13:
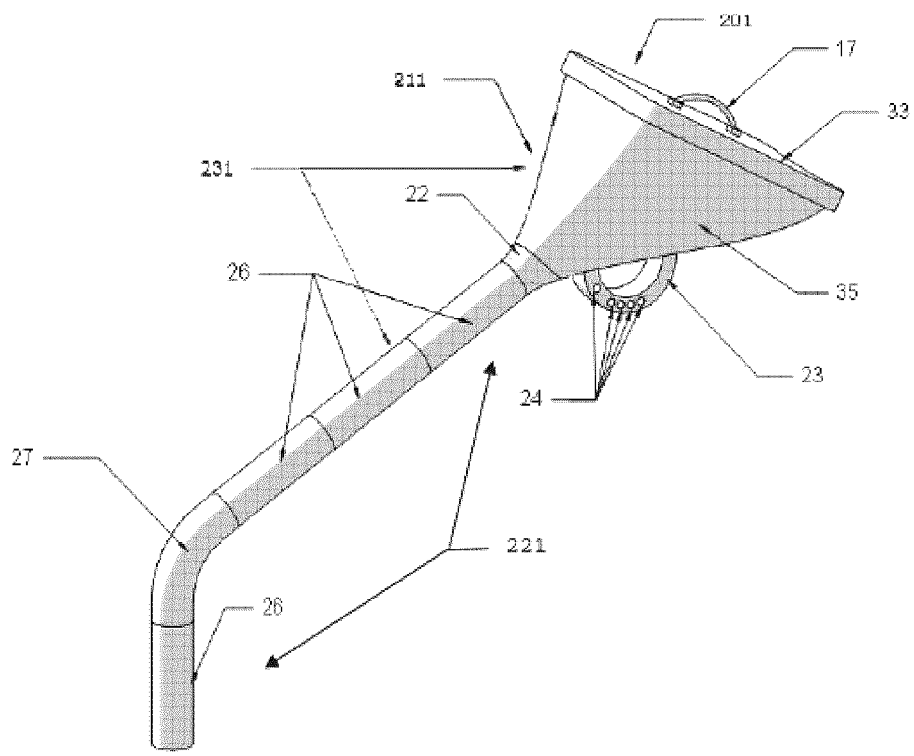
FIG. 13 depicts a perspective side view of Component IIb (the conduit) of device 201 for drainage of contents of an ostomy pouch in accordance with embodiments of the present disclosure.
Figure 14:
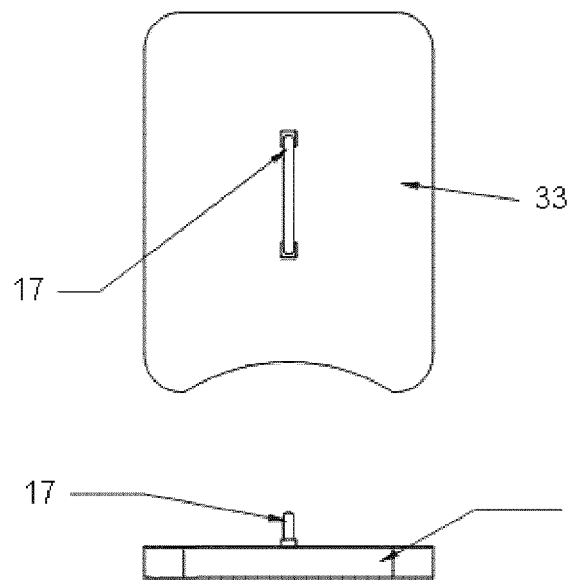
FIG. 14 depicts top and side views of the lid of Component IIb (the conduit) of device 201.

(6) Further coupled to the conduit body along the under-surface of the body, at a point between the body inlet and body outlet, is a pivoting mechanism having a handle defining a fenestrated or curved perforated track that facilitates coupling the body to the extendible shaft (no. 23 and 24 in FIGS. 01, 10 and 12).

(7) The handle is received in the space between the upper sidewalls of the shaft external telescoping sleeve (no. 23 in FIGS. 02 and 04).

(8) A quick release/lock pin (e.g., a commercially available pin) is fitted into the top pair of opposed holes of the external telescoping sleeve sidewalls, and through a chosen fenestration (or the track) in the handle to maintain the body's angle at a desired position (no. 7, FIGS. 01 and 02).

(9) At a point along the under-surface of the conduit body, between the body inlet and body outlet, the body is supported by the pointed tips of the shaft external telescoping sleeve sidewalls (no. 1, FIGS. 01 to 04).

(10) A chute having an upper end coupled to the outlet end of the body (no. 121 and 22, FIG. 01).

(11) A chute having a lower end defining a chute outlet and configured to extend down and forward to direct contents of an ostomy pouch into a waste receptacle (e.g., toilet) (no. 26 in FIGS. 01 and 02).

(12) The lower and upper ends of the chute cooperate to provide a fixed-angle terminal tubing (no. 27 in FIGS. 01 and 02).

(13) An extendable chute (no. 221, FIG. 13) having tubular parts of variable lengths (e.g., a plurality of linear chute segments) connecting above or below an angled chute segment to bring its lower end forward and down as close as possible to the waste receptacle (e.g. toilet) or waterline (no. 26 and 27, FIG. 10).

(14) The chute segments are coupled together using an appropriate joint technique (e.g., a plurality of chute joints) such as waste pipe compression, push-to-connect fitting, a twist-lock feature, or frictionally coupled together like the wand of a vacuum cleaner.

As depicted in the Figures, an example implementation of Component IIb of device 201 (the conduit no. 231, FIG. 13) includes:

(1) A detachable lid having a quasi-rectangular contour (no. 33, FIGS. 13 and 14), a curved handle attached to the lid upper surface (no. 17, FIG. 14) and a downward rim to securely cover to engage the upper end of the body defining the body inlet.

(2) An upper end of the body defining a quasi-rectangular inlet (no. 291, FIG. 15) having rounded edges and at least one curved side to fit against the patient's abdominal wall.

Figure 15:
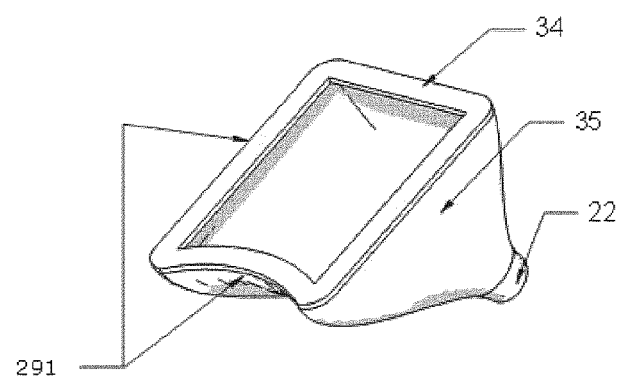
FIG. 15 depicts an angled rear perspective view of the body of Component IIb (the body) of device 201.
Figure 16:
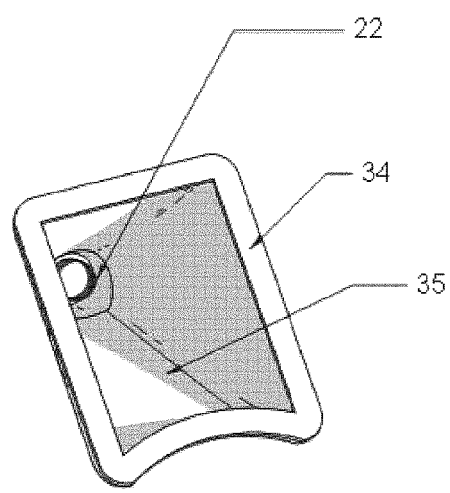
FIG. 16 depicts an angled top perspective view of the body of Component IIb (the body) of device 201.
Figure 17:
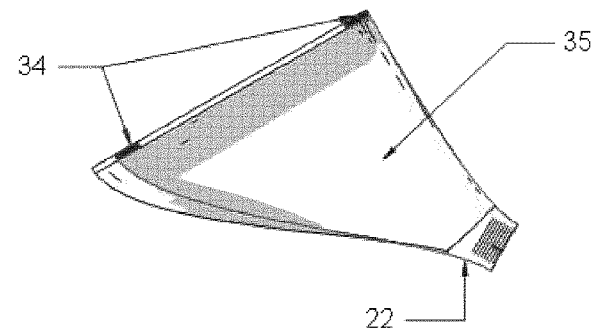
FIG. 17 depicts a side diagrammatic view of the body of Component IIb (the body) of device 201.

(3) The contour of the upper end of the body defining the body inlet further defines a rim (splash guard) around the periphery of the body inlet that extends towards the center of the body, the rim being configured to obstruct splash-back of the contents of the ostomy pouch during drainage (no. 34, FIGS. 15 to 17).

(4) The body is also sized and shaped to conform to the patient's abdomen, having a funnel shaped body with a curved back (no. 35, FIGS. 15 to 17) to receive the ostomy pouch while it is still attached to the patient.

(5) The lower end of the body defines a narrower circular body outlet (no. 22, FIGS. 13, 15 to 17 and 19).

(6) The remainder of the Component IIb, including the pivotal mechanism coupling the body to the extendible shaft and the chute are substantially identical to those described for Component IIa of device 101 (no. 141 and 121, FIG. 01).

Assembly and positioning of a device for sanitary drainage of contents of an ostomy pouch into a waste receptacle (e.g. toilet) may include one or more of the following:

(1) Both the "front" and the "back" of the device are labeled according a patient's orientation and point of view during use.

(2) The back of the device faces the ostomy site, and its front end faces the receptacle (e.g., toilet).

(3) The patient, or an assistant, place the device in a convenient location and appropriate orientation close to a toilet (or any other equivalent waste receptacle).

(4) Height of the extendible shaft is adjusted to the desired level and secured in place using, for example, a quick lock/release pin.

(5) Angle of the body of the device is adjusted to bring the contour of the body inlet against the abdominal wall close to the stoma pouch level.

(6) The angled position of the body is secured using, for example, a quick lock/release pin passing transversely through the upper pair of holes of the sidewalls of the external telescoping sleeve and a chosen hole in the, for example, curved fenestrated handle of the device attached under the body.

(7) The chute is positioned over the waste receptacle (e.g., toilet) rim so that Components I and II (stand and conduit) of the device straddle the receptacle.

(8) The fixed-angled end of the chute may be extended down as close to the waste receptacle (e.g., toilet waterline) as possible by using tubular parts of variable lengths (e.g., a plurality of linear chute segments) above or below an angled chute segment to bring the chute lower end as close as possible to the receptacle and its waterline.

(9) The chute segments are coupled together using an appropriate joint technique (e.g., chute joints) such as waste pipe compression, push-to-connect fitting, a twist-lock feature, or frictionally coupled together, for example like the wand of a vacuum cleaner.

Disassembling of a device for sanitary drainage of contents of an ostomy pouch into a waste receptacle may include one or more of the following:

(1) Top component II (conduit) disassembling, where (1a) the, for example, quick lock/release pin holding the, for example, curved fenestrated body handle in position is pulled out, (1b) after removal of the body, the pin is re-inserted in its place to avoid its accidental loss, and (1c) the chute segments could optionally be disconnected from the body and/or from each other or left attached; and (2) Lower component I (the stand) disassembling, where (2a) the, for example, wingnut and opposite nut securing the lever end circles in position are unscrewed to allow the lever to drop down to embrace the front wall of the external telescoping sleeve, (2b) after folding the lever down, the, for example, wingnut and associated nut are re-screwed again in place to avoid their accidental loss during transportation, (2c) the longitudinally moveable bracket anchoring the shaft external telescoping sleeve is retracted up and disengaged from the base by pulling it up, (2d) the horizontally slidable lock assembly is pushed back (deployed) to engage and hold the curved upper end of the longitudinally moveable bracket preventing it from sliding down.

(2e) the, for example, quick lock/release pin holding the external and internal telescoping sleeves is pulled out, (2f) the external telescoping sleeve is pushed down over the internal telescoping sleeve (collapsing the extendible shaft length), (2g) the base is folded up against the external telescoping sleeve by pivoting the shaft comprising the external and internal telescoping sleeves relative to the base such that it is received and engaged by the two brackets fixed to the upper surface of the base.

Figure 20:
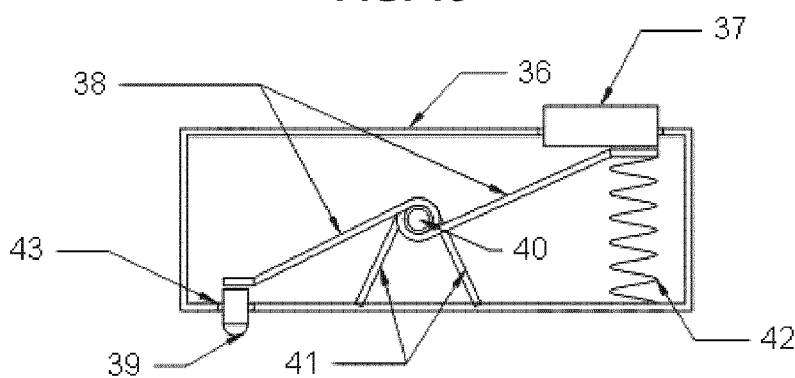
FIG. 20 depicts a diagrammatic side view of a quick lock/release assembly in accordance with an embodiment of the present disclosure.

(2h) the quick lock/release pin is re-inserted in the lowermost opposed adjoining external and internal telescoping sleeve holes and the two brackets fixed to the base, With reference to the Figures, particularly FIG. 20 and the elements no. 36 to 43, there is depicted another example implementation of a quick lock/release assembly for adjusting the length/height of the extendible shaft of the device. The Component I (the stand) parts remain identical to the foregoing detailed embodiment of Component I except for the following differences:

(1) A locking assembly, in a separate enclosure, is attached to one side of the external telescoping sleeve of the extendible shaft at an appropriate distance above the base of the device (FIG. 20).

(2) The locking assembly is manually activated through a clearly labeled quick lock/release push button (no. 37, FIG. 20) to secure the position of the external and internal telescoping sleeves relative to each other for height or length adjustment of the extendible shaft, (3) The locking assembly houses an angled metal strip supported by, and pivoting around a heavy rod (pivot) located at a midpoint between the front and tail ends of the metal strip (no. 38, FIG. 19).

(4) A heavy transverse rod (pivot), around which the metal strip winds and pivots, allows a seesaw action activated by pressing or releasing the push button (no. 40, FIG. 19).

(5) The pivot has an underlying support (no. 41, FIG. 20).

(6) The front end of the metal strip is coupled to a pin attached to its undersurface (no. 39, FIG. 20).

(7) The pin is directed through a hole of appropriate size in the external telescoping sleeve towards the adjoining internal telescoping sleeve (no. 43, FIG. 20).

(9) A longitudinal row of appropriately spaced holes/fenestrations are made in one side of the internal telescoping sleeve (no. 30, FIG. 05), to receive the pin from the locking assembly attached to the adjoining external sleeve (no. 39, FIG. 19) and lock the shaft at the desired length/height.

(8) The assembly has a circular spring coupled up to the undersurface of the metal strip tail end and to the underlying the external telescoping sleeve sidewall to which the assembly is attached.

(10) Like a seesaw in action, when the tail end of the metal strip is pushed up by the spring action (no. 42, FIG. 20), the front end of the metal strip would push the pin down in the opposite direction to engage a chosen adjoining internal sleeve hole.

(11) Manual pressure exerted over the push button depresses the tail end of the metal strip and the underlying spring to disengage the pin (no. 39, FIG. 20) from the hole in the adjoining internal telescoping sleeve resembling a seesaw action.

(12) After disengaging the pin, the slidable external telescoping sleeve can be moved up or down along the internal telescoping sleeve to achieve the desired extendible shaft height/length.

(13) To securely adjust and hold the two telescoping sleeves at the desired/height length, manual pressure is taken off the push button, allowing the pin to engage the chosen adjoining internal telescoping sleeve side hole.

(14) The quick locking assembly may require more elaborate manufacturing of the device, but may offer an ergonomic improvement over the use of quick lock/release pins to adjust and steady the shaft sleeves at the desired height/length.

(15) When using this alternative implementation for assembling and disassembling the device, the same steps described for Component I (stand) are used except that the height/length of the shaft would be adjusted and secured in place using the locking assembly rather than the quick lock/release pins.

An example method for using a device for sanitary drainage of contents of an ostomy pouch into a waste receptacle may include one or more of the following:

(1) Optionally, a cover of the waste receptacle (e.g., toilet seat) is raised; and the lid of the device is removed.

(2) A lower end of the ostomy pouch, attached to the patient, is opened to drain its contents into the body of the device.

(3) After emptying the waste contents, the open lower end of the ostomy pouch is flushed gently with water from, for example, a jug with a nozzle, a squeeze-spraying bottle, or any alternative water source.

(4) Toilet paper, for example, may be used to wipe dry the lower end of the ostomy pouch before closing it.

(5) The interior of the device and its contents may be flushed with water into the waste receptacle (e.g., toilet) using the same jug or other water source.

(6) An antiseptic spray may be used periodically for disinfecting the device.

(7) The device may be covered with its lid for storage, and the waste receptacle (e.g., toilet seat) may be covered.

(8) The waste disposer (e.g., toilet) may be flushed.

Advisable hygienic and sanitary considerations for ostomy patients may include one or more of the following:

(I) A device as described herein is may be used with a waste receptacle where a source of water is available for cleaning.

(II) The patient and/or assistant may use protective disposable nitrile (latex-free) gloves and masks, especially if they are immune-compromised such as diabetics and cancer patients receiving chemotherapy.

(III) The patient and/or assistant may need to wash their hands, or use alcohol-based sanitizer after emptying the pouch.

(IV) Odor control may be achieved by instilling lubricating deodorant in the pouch, or by using deodorant spray, scented candle or incense in the waste disposal facility.

CONCLUSION

A device for drainage of contents of an ostomy pouch into a receptacle as described herein provides a material advance for sanitary disposal of biological wastes from ostomy pouches. The device provides mobile ostomy patients a safe, convenient, ergonomic, hygienic and sanitary way to empty their ostomy pouches. It allows patients to dispose of their biological waste from a comfortable position, for example, standing independently.

The distance between a patient, while seated on a receptacle such as a toilet, to said receptacle's interior (e.g., waterline) is much shorter than that between an abdominal wall ostomy level and a conventional receptacle's interior (e.g., a waterline/seal). The device allows mobile patients to stand up straight and let their ostomy pouch contents drop a long distance, from the higher abdominal wall stoma level (stoma meaning ostomy mouth) into the bottom of a fixed height conventional toilet containing a water seal (for example), with a reduced risk of waste contamination or splash-back.

Emptying waste-containing ostomy pouches in a standing position using the herein described device having an adjustable height/extendible length and adjustable angle in conjunction with a receptacle, such as a toilet, offers mobile patients a solution for ostomy pouch drainage. The features of the device can provide a customized way to bridge the long physical gap between an ostomy pouch and a receptacle by bringing the body of the device as described herein, at a desired angle and height, up to an ostomy site, with the chute angled end down to the receptacle (e.g., toilet waterline).

In the preceding description, for purposes of explanation, numerous details are set forth in order to provide a thorough understanding of the embodiments. However, it will be apparent to one skilled in the art that these specific details are not required. The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A device for sanitary drainage of contents of an ostomy pouch into a toilet, the device comprising
   a base;
   an extendible shaft configured to provide adjustment of a length of the shaft, the extendible shaft having a lower end coupled to the base and having an upper end;
   a body configured to receive the ostomy pouch while the pouch is attached to a mobile patient in an upright position, the body having an upper end defining a body inlet configured to receive the ostomy pouch, the body having a lower end defining a body outlet configured to direct the contents of the ostomy pouch out of the body;
   a pivoting mechanism pivotally coupling the lower end of body to the upper end of the extendible shaft, the pivoting mechanism engaging the body between the body inlet and the body outlet to provide adjustment of an angle between the body and the extendible shaft; and
   a chute coupled to the body outlet and configured to receive the contents of the ostomy pouch from the body and to direct the contents into the receptacle while the pouch is attached to the mobile patient, the chute having an upper end coupled to the outlet end of the body, the upper end of the chute defining a chute inlet configured to direct the contents of the ostomy pouch into the chute, and having a lower end defining a chute outlet configured to direct the contents out of the chute and into the receptacle while the pouch is attached to the mobile patient.

2. The device of claim 1, wherein the chute comprises an extendible chute.

3. The device of claim 2, wherein the extendible chute comprises a plurality of chute segments coupled together via a plurality of chute joints to configure the chute to a pre-determined length.

4. The device of claim 3, wherein the plurality of chute segments comprise a plurality of linear chute segments and an angled chute segment cooperating to provide a fixed angle between the upper end and the lower end of the chute.

5. The device of claim 1, wherein the shaft comprises at least two telescoping sleeves.

6. The device of claim 5, wherein the at least two telescoping sleeves are configured to couple together at a plurality of engagement points.

7. The device of claim 1, wherein the pivoting mechanism comprises a handle defining a perforated curved track, the handle pivotally coupling the body to the upper end of the shaft.

8. The device of claim 7, wherein the handle is configured to couple the upper end of the shaft at a plurality of engagement points.

9. The device of claim 1, wherein the upper end of the body defining the body inlet further defines a rim around the periphery of the body inlet that extends towards the center of the body, the rim being configured to obstruct splash-back of the contents of the ostomy pouch during drainage.

10. The device of claim 1, further comprising a lid configured to engage and cover the upper end of the body defining the body inlet.

11. The device of claim 1, further comprising a lever coupled to the upper end of the chute and the upper end of the shaft, the lever enabling further adjustment of an angle between the chute and the shaft.

12. The device of claim 1 further comprising a moveable bracket attached to the extendible shaft to engage a slot in the base to secure the shaft in a vertical position when the device is in use.

13. The device of claim 12, further comprising a slidable lock assembly coupled to the upper end of the extendible shaft, the slidable lock assembly being configured to engage the moveable bracket and secure the moveable bracket in a position disengaged from the slot in the base.

14. The device of claim 1, wherein the base comprises two brackets fixed to an upper surface of the base.

15. The device of claim 1, wherein the base defines a plurality of fenestrations and further comprises a plurality of pedestals.

16. The device of claim 1 further comprising a quick lock/release pin configured to engage with the shaft to facilitate adjustment of the length of the shaft.

17. The device of claim 1 further comprising a quick lock/release assembly including a pin, a push button, and a pivot coupled to both the pin and the push button to facilitate adjustment of the length of the shaft.

18. The device of claim 1, wherein the body is sized and shaped to contour to the abdomen of a patient.

19. The device of claim 18, wherein at least a portion of the body has a curved periphery.

20. A device for drainage of contents of an ostomy pouch, the device comprising:
- a base;
  - an extendible shaft configured to provide adjustment of a length of the shaft, the extendible shaft having a lower end coupled to the base and having an upper end;
  - a body configured to receive the ostomy pouch while the pouch is attached to a patient, the body having an upper end defining a body inlet configured to receive the ostomy pouch, the body having a lower end defining a body outlet configured to direct the contents of the ostomy pouch out of the body;
  - a pivoting mechanism pivotally coupling the lower end of body to the upper end of the extendible shaft, the pivoting mechanism engaging the body between the body inlet and the body outlet to provide adjustment of an angle between the body and the extendible shaft; and
  - a chute coupled to the body outlet and configured to receive the contents of the ostomy pouch from the body while the pouch is attached to the patient, the chute having an upper end coupled to the outlet end of the body, the upper end of the chute defining a chute inlet configured to direct the contents of the ostomy pouch into the chute, and having a lower end defining a chute outlet configured to direct the contents out of the chute while the pouch is attached to the patient.

* * * * *